US012781217B2

(12) United States Patent
Surkov et al.

(10) Patent No.: US 12,781,217 B2
(45) Date of Patent: Nov. 3, 2026

(54) METHOD FOR ISOLATING AND ANALYZING CELL FREE DNA

(71) Applicant: SANTERSUS AG, Zürich (CH)

(72) Inventors: Kirill Surkov, Saint Petersburg (RU); Simon Tallett, Forch (CH); Andrew Aswani, London (GB)

(73) Assignee: SANTERSUS AG, Zürich (CH)

( * ) Notice: Subject to any disclaimer, the term of this patent is extended or adjusted under 35 U.S.C. 154(b) by 1041 days.

(21) Appl. No.: 17/766,347

(22) PCT Filed: Oct. 2, 2020

(86) PCT No.: PCT/IB2020/000817

§ 371 (c)(1),
(2) Date: Apr. 4, 2022

(87) PCT Pub. No.: WO2021/064463

PCT Pub. Date: Apr. 8, 2021

(65) Prior Publication Data

US 2024/0052334 A1 Feb. 15, 2024

Related U.S. Application Data

(60) Provisional application No. 62/910,840, filed on Oct. 4, 2019.

(51) Int. Cl.
*C12Q 1/6806* (2018.01)
*C12N 15/10* (2006.01)

(52) U.S. Cl.
CPC ..... *C12N 15/1013* (2013.01); *C12N 15/1006* (2013.01); *C12Q 1/6806* (2013.01)

(58) Field of Classification Search
CPC .................................................... C12Q 1/6806
See application file for complete search history.

(56) References Cited

U.S. PATENT DOCUMENTS

| | | | |
|---|---|---|---|
| 4,824,432 | A | 4/1989 | Skurkovich et al. |
| 6,046,046 | A | 4/2000 | Hassanein |
| 6,080,404 | A | 6/2000 | Branham |
| 6,528,057 | B1 | 3/2003 | Ambrus et al. |
| 6,774,102 | B1 | 8/2004 | Bell et al. |
| 7,612,032 | B2 | 11/2009 | Genkin et al. |
| 8,388,951 | B2 | 3/2013 | Genkin et al. |
| 8,431,123 | B2 | 4/2013 | Genkin et al. |
| 8,535,663 | B2 | 9/2013 | Genkin et al. |
| 8,916,151 | B2 | 12/2014 | Genkin et al. |
| 9,128,086 | B2 | 9/2015 | Bawden et al. |
| 9,248,166 | B2 | 2/2016 | Genkin et al. |
| 9,364,601 | B2 | 6/2016 | Ichim et al. |
| 9,402,944 | B2 | 8/2016 | Selden et al. |
| 9,642,822 | B2 | 5/2017 | Wagner et al. |
| 10,639,405 | B2 | 5/2020 | Kiriyama |
| 10,746,746 | B2 | 8/2020 | Eccleston et al. |
| 12,053,567 | B2 | 8/2024 | Surkov et al. |
| 2007/0092509 | A1 | 4/2007 | Mittra et al. |
| 2008/0004561 | A1 | 1/2008 | Genkin et al. |
| 2009/0117099 | A1 | 5/2009 | Esmon et al. |
| 2011/0034370 | A1* | 2/2011 | Gross ...................... A61P 29/00 435/235.1 |
| 2011/0125286 | A1 | 5/2011 | Selden et al. |
| 2012/0226258 | A1 | 9/2012 | Otto et al. |
| 2012/0301487 | A1 | 11/2012 | Mittra et al. |
| 2013/0320858 | A1 | 12/2013 | Deery et al. |
| 2014/0099293 | A1 | 4/2014 | Mittra et al. |
| 2017/0035955 | A1 | 2/2017 | Eliaz |
| 2018/0024141 | A1 | 1/2018 | Micallef et al. |
| 2018/0266951 | A1* | 9/2018 | Spero ................ B01L 3/502761 |
| 2020/0261639 | A1 | 8/2020 | Surkov |

FOREIGN PATENT DOCUMENTS

| | | | |
|---|---|---|---|
| CN | 105319374 | A | 2/2016 |
| EP | 1666055 | A1 | 6/2006 |
| EP | 2390662 | A1 | 11/2011 |
| JP | 2004350502 | | 12/2004 |
| RU | 2441674 | C1 | 10/2012 |
| TW | 201819922 | | 6/2018 |
| WO | 2005025650 | A1 | 3/2005 |
| WO | 2007049286 | | 3/2007 |
| WO | 2008047364 | A2 | 4/2008 |
| WO | 2013084002 | | 6/2013 |
| WO | 2014020564 | A1 | 2/2014 |
| WO | 2014169043 | A1 | 10/2014 |
| WO | 2015161094 | A1 | 10/2015 |
| WO | 2017049279 | A1 | 3/2017 |

(Continued)

OTHER PUBLICATIONS

Office Action issued Nov. 21, 2022 in connection with U.S. Appl. No. 16/648,045.

European Search Report issued May 18, 2022 in connection with EP Application No. 21209611.9.

Licht et al., "Plasma levels of nucleosomes and nucleosome-autoantibody complexes in murine lupus: Effects of disease progression and lipopolysaccharide administration", Athritis and Rheumatism, vol. 44, No. 6, Jun. 1, 2001, pp. 1320-1330.

Bauden et al., "Cirulating nucleosome as epigenic biomarkers in pancreatic cancer", Clinical Epigentics, Biomed Central Ltd., London, UK, vol. 7, No. 1, Oct. 7, 2015, p. 106.

Atamaniuk, J. et al.,"Apoptotic Cell-Free DNA Promotes Inflammation in Haemodialysis Patients" Nephrol Dial Transplant (2012) vol. 27, pp. 902-905.

(Continued)

*Primary Examiner* — Jonathan M Hurst
(74) *Attorney, Agent, or Firm* — Troutman Pepper Locke LLP

(57) ABSTRACT

The invention provides methods of detecting substantially all types of cell free DNA (cfDNA) in biological samples, including nucleosome-bound cfDNA, exosome-bound cfDNA and unbound cfDNA (including double stranded DNA (dsDNA), single stranded DNA (ssDNA) and oligonucleotides), for diagnosis, monitoring and treatment of diseases caused by, or correlated with, increased levels of cfDNA.

13 Claims, No Drawings

Specification includes a Sequence Listing.

(56) References Cited

FOREIGN PATENT DOCUMENTS

| | | | |
|---|---|---|---|
| WO | 2017068371 | A1 | 4/2017 |
| WO | 2017137495 | A1 | 8/2017 |
| WO | 2018119422 | | 6/2018 |
| WO | 2019053243 | | 3/2019 |
| WO | 2021038010 | A1 | 3/2021 |
| WO | 2021064463 | | 4/2021 |

OTHER PUBLICATIONS

Brockers, K. et al., "Histone H1, the Forgotten Histone" Epigenomics (2019) vol. 11, No. 4, pp. 363-366.
Cao, H. et al., "Circulatory Mitochondrial DNA is a Pro-Inflammatory Agent in Maintenance Hemodialysis Patients" PLOS One (2014) vol. 9, No. 12, 14 pages total.
Czamanski-Cohen, J. et al., "Increased Plasma Cell-Free DNA is Associated with Low Pregnancy Rates Among Women Undergoing IVF-Embryo Transfer" Reproductive BioMedicine Online (2013) vol. 26, pp. 36-41.
Davis, JC et al., "Recombinant Human Dnase I (rhDNase) in Patients with Lupus Nephritis" Lupus (1999) vol. 8, pp. 68-76.
Gunjan, A. et al., "Effects of H1 Histone Variant Overexpression on Chromatin Structure" The Journal of Biological Chemistry (1999) vol. 274, No. 53, pp. 37950-37956.
Hergeth, S.P. et al., "The H1 Linker Histones: Multifunctional Proteins Beyond the Nucleosomal Core Particle" EMBO Reports (2015) vol. 16, No. 11, pp. 1439-1453.
Kumar, P. et al., "Normal and Cancerous Tissues Release Extrachromosomal Circular DNA (eccDNA) into the Circulation" Mol Cancer Res (2017) vol. 15, No. 9, pp. 1197-1205.
Kusaoi, M. et al., "Separation of Circulating MicroRNAs Using Apheresis in Patients with Systemic Lupus Erythematosus" Therapeutic Apheresis and Dialysis (2016) vol. 20, No. 4, pp. 358-353.
Lintern, K.B. et al., "Immobilisation of Lactate Oxidase and Deoxyribonuclease I for Use Within a Bio-Artificial Liver Assist Device for the Treatment of Acute Liver Failure" University College London (2013) 209 pages total.
Simakova, E.S. et al., "An Experimental Support of the Use of Immobilized Decoxyribonuclease of Type I in the Treatment of Systemic Lupus Erythematosus" Abstract of Medical Science PHD Thesis (2011) 53 pages total.
Smith, B.J. et al., "Structural Homology Between a Mammalian H1 Subfraction and Avian Erythrocyte-Specific Histone H5" FEBS Letters (1980) vol. 112, No. 1, pp. 42-44.
Su, K-Y et al., "Mutational Monitoring of EGFR T790M in cfDNA for Clinical Outcome Prediction in EGFR-Mutant Lung Adenocarcinoma" PLOS One (2018) vol. 13, No. 11, 15 pages total.
"Terman, D.S. et al., ""Degardation of DNA and DNA: Anti-DNA Complexes by Extracorporeal Circulation over Nuclease Immobilized on Nylon Microspheres"" Abstract: The American Society of Nephrology (1975) 2 pages total."
Terman, S.D. et al., ""Degradation of Circulating DNA by Extracorporeal Circulation over Nuclease Immobilized on Nylon Microcapsules" The Journal of Clinical Investigation (1976) vol. 57, pp. 1201-1212."
Terrell, J. et al., "Enrichment of Circulating Tumor DNA from Cell-Free DNA of Hematopoietic Origin" Journal of Clinical Oncology (2020) vol. 38, Issue 15, supplement, 3 pages total.
Trofimenko, A.S. et al., "Extracorporal Correction of Deteriorations of Catabolismof Nucleoproteins in a Model of Systemic Lupus Erythematosus. Efficiency and Safety Assessment in the Acute Experiment" Biomedical Chemistry (2015) vol. 61, pp. 622-627.
Tullis, R.H. et al., "Affinity Hemodialysis for Antiviral Therapy with Specific Application to HIV" Journal of Theoretical Medicine (2002) vol. 4, No. 3, pp. 157-166.
Yasuda, T. et al., "Abrupt Pubertal Elevation of Dnase I Gene Expression in Human Pituary Gland of Both Sexes" FEBS Letters (2002) vol. 510, pp. 22-26.
Zachariah, R. et al., "Circulating Cell-Free DNA as a Potential Biomarker for Minimal and Mild Endometriosis" Reproductive Biomedicine Online (2009) vol. 18, No. 3, pp. 407-411.
Communication (pursuant to Article 94(3) EPC) issued by the European Patent Office in European Application No. 18773736.6 dated Mar. 9, 2021, 4 pages total.
Office Action issued Sep. 13, 2021 in connection with Japanese Patent Application No. 2020-537046.
Office Action issued Dec. 2, 2021 in connection with Russian Application No. 2020113528.
G. Tokareva Issledovanye fetalnoy i materinskoy vnekletochnoy DNK pri normalnoy beremennosti i narusheniyakh razvitiay ploda. Abstract of the thesis. Tomsk, 2006, p. 19.
European Search Report issued Feb. 15, 2022 in connection with EP Application No. 21209617.
Atkinson A. et al., "Precipitation of nucleic acids with polyethyleneimine and the chromatography of nucleic acids and proteins on immobilised polyethyleeneimine", Biochimica Et Biophysica ACTA, Amsterdam, NL, vol. 308, No. 1, Apr. 21, 1973, pp. 41-52.
Lee J. et al., "Nucleic acid-binding polypers as anti-inflammatory agents", Proceedings of the National Academy of Sciences, vol. 108, No. 34, Aug. 23, 2011, pp. 14055-14060.
Office Action issued Mar. 15, 2022 in connection with Russian Application No. 2020113528.
Marleau A.M. et al., "Exosome removal as a therapeutic adjuvant in cancer", Journal of Translational Medicine, 2012, 10: 134, pp. 1-12.
International Search Report and Written Opinion mailed Jan. 19, 2021 in connection with International Application No. PCT/IB2020/000817.
Lau P. P. et al., "A Rapid Method for the Purification of Supercoiled PM2 DNA by Affinity Chromatography on H1 Histone Covalently Coupled to Agarose", Biochimica et Biophysica Acta, 563 (1979) pp. 313-319.
Yu S. et al., "Chromatography of Different Forms of DNA on Immobilized Histone Columns", Biochimica et Biophysica Acta, 517 (1978) pp. 31-42.
Communication (International Preliminary Report on Patentability) issued by the International Searching Authority in International Application No. PCT/EP2018/075014 dated Jan. 9, 2019.
Communication (International Search Report) issued by the International Searching Authority in International Application No. PCT/EP2018/075014 dated Mar. 24, 2020.
Fukama, T., "Gene Therapy and Regulation" Gene Therapy and Regulation (2000) 2 pages total.
Wang, Z. et al., "Water-Soluble Adsorbent [beta]-cyclodextrin-grafted Polyethyleneimine for Removing Bilirubin from Plasma" Transfusion and Apheresis Science (2012) vol. 47, No. 2, pp. 159-165.
Tanaka et al., "Expression and purification of recombinant human histones" Methods, 2004, 33(1):3-11.
Dyer et al., "Reconstitution of Nucleosome Core Particles from Recombinant Histones and DNA" Methods Enzymol., 2003, 375:23-44.
Ross et al., "Optimization of ligand presentation for immunoadsorption using star-configured polythylene glycols" J Biomed Mater Res, 2000, 51:29-36.
International Search Report and Written Opinion mailed Apr. 18, 2023 in connection with PCT/IB2022/000665.
Office Action issued Feb. 23, 2023 in connection with U.S. Appl. No. 16/648,045.
Office Action issued Aug. 25, 2023 in connection with U.S. Appl. No. 17/971,016.
Muhlbacher, F. et al., "Preservation Solutions for Transplantation", Trans. Proc., 1999, pp. 2069-2070.
Weissenbacher, A. et al., "The future of organ perfusion and re-conditioning", Trans, Inct., 2019, vol. 32: pp. 586-297.
Lui et al. "Predominant Hematopoietic Origin of Cell-freeDNA in Plasma and Serum after Sex-mismatchedBone Marrow Transplantation", Clin Chem. 48(3):421-7, 2002.
Moss et al. "Comprehensive human cell-type methylation atlasreveals origins of circulating cell-free DNA in healthand disease", Nature Communications vol. 9, 5068, 2018.

(56) References Cited

OTHER PUBLICATIONS

Laurent et al. "Absolute measurement of the tissue originsof cell-free DNA in the healthy state andfollowing paracetamol overdose", BMC Medical Genomics vol. 13, 60, 2020.
Sun et al. "Plasma DNA tissue mapping by genome-widemethylation sequencing for noninvasive prenatal,cancer, and transplantation assessments", PNAS, vol. 112, No. 40, 2015.
Camprubí-Rimblas et al. "Anticoagulant therapy in acute respiratory distress syndrome", Ann Transl Med. 6(2): 36, 2018.
Noda et al. "Impact of Heparin on EndothelialGlycocalyx in Lung Grafts during ExVivo Lung Perfusion", J Heart Lung Transplantation, 2021; 40: S344-345, Abstract.
International Preliminary Report on Patentability issued Apr. 5, 2022 in connection with PCT Application No. PCT/IB2020/000817.
International Search Report and Written Opinion mailed Sep. 19, 2022 in connection with PCT/IB2022/000192.
Thalin Charlotte et al., "Quantification of citrullinated histones: Development of an improved assay to reliability quantify nucleosomal H3Cit in human plasma" Journal of Thrombosis and Haemostasis, vol. 18, No. 10, Aug. 8, 2020, pp. 2732-2743.
Tsourouktsoglou Theodora-Dorita et al., "Histones, DNA, and Citrullination Promote Neutrophil Extracellular Trap Inflammation by Regulating the Localization and Activation of TLR4", Cell Reports, vol. 31, No. 5, May 1, 2020, pp. 107602.
First Office Action issued in Application No. CN 201880067725.9 mailed Feb. 27, 2023; with English Translation; 6 pages.
Communication pursuant to Article 94(3) EPC issued in EP Application No. 21209617.6 on Sep. 16, 2025.
Communication (Written Opinion) issued by the International Searching Authority in International Application No. PCT/ EP2018/ 075014 dated Jan. 9, 2019, 6 pages total.
Hudecova et al., Characteristics, origin, and potential for cancer diagnostics of ultrashot plasma cell-free DNA, Genome Research (2022), 32:215-227.
Wang et al., Ultra-short cell-free DNA fragments enhance cancer early detection in a multi-analyte blood test combining mutation, protein and fragmentomics, Clin Chem Lab Med (2024), 62(1): 168-177.
Cheng et al., Distinct Features of Plasma Ultrashort Single-Stranded Cell-Free DNA as Biomarkers for Lung Cancer Detection, Clinical Chemistry (2023), 69(11): 1270-1282.
Tajima et al., Significance of Antibody Orientation Unraveled: Well-Oriented Antibodies Recorded High Binding Affinity, Analytical Chemistry (2011), 83:1969-1976.
White et al., A quantitative investigation of linker histone interactions with nucleosomes and chromatin, Scientific Reports (Jan. 11, 2016), 6(19122): 1-14.

* cited by examiner

SEQUENCE LISTING

```
<160> NUMBER OF SEQ ID NOS: 7

<210> SEQ ID NO 1
<211> LENGTH: 221
<212> TYPE: PRT
<213> ORGANISM: Homo sapiens

<400> SEQUENCE: 1

Met Ser Glu Thr Ala Pro Leu Ala Pro Thr Ile Pro Ala Pro Ala Glu
1               5                   10                  15

Lys Thr Pro Val Lys Lys Lys Ala Lys Lys Ala Gly Ala Thr Ala Gly
```

```
            20                  25                  30

Lys Arg Lys Ala Ser Gly Pro Pro Val Ser Glu Leu Ile Thr Lys Ala
        35                  40                  45

Val Ala Ala Ser Lys Glu Arg Ser Gly Val Ser Leu Ala Ala Leu Lys
    50                  55                  60

Lys Ala Leu Ala Ala Ala Gly Tyr Asp Val Glu Lys Asn Asn Ser Arg
65                  70                  75                  80

Ile Lys Leu Gly Leu Lys Ser Leu Val Ser Lys Gly Thr Leu Val Gln
                85                  90                  95

Thr Lys Gly Thr Gly Ala Ser Gly Ser Phe Lys Leu Asn Lys Lys Ala
            100                 105                 110

Ala Ser Gly Glu Gly Lys Pro Lys Ala Lys Lys Ala Gly Ala Ala Lys
        115                 120                 125

Pro Arg Lys Pro Ala Gly Ala Ala Lys Lys Pro Lys Lys Val Ala Gly
    130                 135                 140

Ala Ala Thr Pro Lys Lys Ser Ile Lys Lys Thr Pro Lys Lys Val Lys
145                 150                 155                 160

Lys Pro Ala Thr Ala Ala Gly Thr Lys Lys Val Ala Lys Ser Ala Lys
                165                 170                 175

Lys Val Lys Thr Pro Gln Pro Lys Lys Ala Ala Lys Ser Pro Ala Lys
            180                 185                 190

Ala Lys Ala Pro Lys Pro Lys Ala Ala Lys Pro Lys Ser Gly Lys Pro
        195                 200                 205

Lys Val Thr Lys Ala Lys Lys Ala Ala Pro Lys Lys Lys
    210                 215                 220


<210> SEQ ID NO 2
<211> LENGTH: 193
<212> TYPE: PRT
<213> ORGANISM: Homo sapiens

<400> SEQUENCE: 2

Thr Glu Asn Ser Thr Ser Ala Pro Ala Ala Lys Pro Lys Arg Ala Lys
1               5                   10                  15

Ala Ser Lys Lys Ser Thr Asp His Pro Lys Tyr Ser Asp Met Ile Val
            20                  25                  30

Ala Ala Ile Gln Ala Glu Lys Asn Arg Ala Gly Ser Ser Arg Gln Ser
        35                  40                  45

Ile Gln Lys Tyr Ile Lys Ser His Tyr Lys Val Gly Glu Asn Ala Asp
    50                  55                  60

Ser Gln Ile Lys Leu Ser Ile Lys Arg Leu Val Thr Thr Gly Val Leu
65                  70                  75                  80

Lys Gln Thr Lys Gly Val Gly Ala Ser Gly Ser Phe Arg Leu Ala Lys
                85                  90                  95

Ser Asp Glu Pro Lys Lys Ser Val Ala Phe Lys Lys Thr Lys Lys Glu
            100                 105                 110

Ile Lys Lys Val Ala Thr Pro Lys Lys Ala Ser Lys Pro Lys Lys Ala
        115                 120                 125

Ala Ser Lys Ala Pro Thr Lys Lys Pro Lys Ala Thr Pro Val Lys Lys
    130                 135                 140

Ala Lys Lys Lys Leu Ala Ala Thr Pro Lys Lys Ala Lys Lys Pro Lys
145                 150                 155                 160

Thr Val Lys Ala Lys Pro Val Lys Ala Ser Lys Pro Lys Lys Ala Lys
                165                 170                 175
```

```
Pro Val Lys Pro Lys Ala Lys Ser Ser Ala Lys Arg Ala Gly Lys Lys
            180                 185                 190

Lys


<210> SEQ ID NO 3
<211> LENGTH: 193
<212> TYPE: PRT
<213> ORGANISM: Anser anser

<400> SEQUENCE: 3

Thr Asp Ser Pro Ile Pro Ala Pro Ala Pro Ala Ala Lys Pro Lys Arg
1               5                   10                  15

Ala Arg Ala Pro Arg Lys Pro Ala Ser His Pro Thr Tyr Ser Glu Met
            20                  25                  30

Ile Ala Ala Ala Ile Arg Ala Asp Lys Ser Arg Gly Gly Ser Ser Arg
        35                  40                  45

Gln Ser Ile Gln Lys Tyr Val Lys Ser His Tyr Lys Val Gly Gln His
    50                  55                  60

Ala Asp Leu Gln Ile Lys Leu Ala Ile Arg Arg Leu Leu Thr Thr Gly
65                  70                  75                  80

Val Leu Lys Gln Thr Lys Gly Val Gly Ala Ser Gly Ser Phe Arg Leu
                85                  90                  95

Ala Lys Gly Asp Lys Ala Lys Arg Ser Pro Ala Gly Arg Lys Lys Lys
            100                 105                 110

Lys Lys Ala Ala Arg Lys Ser Thr Ser Pro Lys Lys Ala Ala Arg Pro
        115                 120                 125

Arg Lys Ala Arg Ser Pro Ala Lys Lys Pro Lys Ala Ala Ala Arg Lys
    130                 135                 140

Ala Arg Lys Lys Ser Arg Ala Ser Pro Lys Lys Ala Lys Lys Pro Lys
145                 150                 155                 160

Thr Val Lys Ala Lys Ser Leu Lys Thr Ser Lys Pro Lys Lys Ala Arg
                165                 170                 175

Arg Ser Lys Pro Arg Ala Lys Ser Gly Ala Arg Lys Ser Pro Lys Lys
            180                 185                 190

Lys


<210> SEQ ID NO 4
<211> LENGTH: 190
<212> TYPE: PRT
<213> ORGANISM: Gallus gallus

<400> SEQUENCE: 4

Met Thr Glu Ser Leu Val Leu Ser Pro Ala Pro Ala Lys Pro Lys Arg
1               5                   10                  15

Val Lys Ala Ser Arg Arg Ser Ala Ser His Pro Thr Tyr Ser Glu Met
            20                  25                  30

Ile Ala Ala Ala Ile Arg Ala Glu Lys Ser Arg Gly Gly Ser Ser Arg
        35                  40                  45

Gln Ser Ile Gln Lys Tyr Ile Lys Ser His Tyr Lys Val Gly His Asn
    50                  55                  60

Ala Asp Leu Gln Ile Lys Leu Ser Ile Arg Arg Leu Leu Ala Ala Gly
65                  70                  75                  80

Val Leu Lys Gln Thr Lys Gly Val Gly Ala Ser Gly Ser Phe Arg Leu
                85                  90                  95

Ala Lys Ser Asp Lys Ala Lys Arg Ser Pro Gly Lys Lys Lys Lys Ala
            100                 105                 110
```

-continued

```
Val Arg Arg Ser Thr Ser Pro Lys Lys Ala Ala Arg Pro Arg Lys Ala
        115                 120                 125

Arg Ser Pro Ala Lys Lys Pro Lys Ala Thr Ala Arg Lys Ala Arg Lys
    130                 135                 140

Lys Ser Arg Ala Ser Pro Lys Lys Ala Lys Lys Pro Lys Thr Val Lys
145                 150                 155                 160

Ala Lys Ser Arg Lys Ala Ser Lys Ala Lys Lys Val Lys Arg Ser Lys
                165                 170                 175

Pro Arg Ala Lys Ser Gly Ala Arg Lys Ser Pro Lys Lys Lys
            180                 185                 190


<210> SEQ ID NO 5
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 5

caacttcatc cacgttcacc                                                   20


<210> SEQ ID NO 6
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 6

tgaggagaca ccgcccac                                                     18


<210> SEQ ID NO 7
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 7

catggtgaaa ccccgtctct a                                                 21
```

METHOD FOR ISOLATING AND ANALYZING CELL FREE DNA

This application is a U.S. National Stage application under 35 U.S.C. § 371 of International Application No. PCT/IB2020/000817, filed Oct. 2, 2020, which claims priority to U.S. Provisional Application No. 62/910,840, filed Oct. 4, 2019, the disclosures of which are herein incorporated by reference in their entirety.

SEQUENCE LISTING

The instant application contains a Sequence Listing which has been submitted electronically in ASCII format and is hereby incorporated by reference in its entirety. Said ASCII copy, created on Sep. 1, 2020, is named 252176_000015_SL.txt and is 8,033 bytes in size.

FIELD OF THE INVENTION

The invention provides methods of isolating and analyzing substantially all types of cell free DNA (cfDNA) in biological samples, including nucleosome-bound cfDNA, exosome-bound cfDNA and unbound cfDNA (including double stranded DNA (dsDNA), single stranded DNA (ssDNA) and oligonucleotides), for diagnosis, monitoring and treatment of diseases caused by, or correlated with, increased levels of cfDNA.

BACKGROUND OF THE INVENTION

Extracellular DNA (eDNA), also called cell free DNA (cfDNA), is present in small amounts in the biofluids of healthy individuals.

Cell-free DNA (cfDNA) serves as an excellent source of DNA-based biomarkers for the detection and monitoring of cancer and other diseases and conditions. An increased level of cfDNA in biofluids (mainly in the blood) is now a widely accepted as a marker for a number of diseases and pathological conditions including but not limited to cancer, metastatic cancer, acute organ failure, organ infarct (including myocardial infarction and ischemic stroke), hemorrhagic stroke, autoimmune disorders, graft-versus-host-disease (GVHD), graft rejection, sepsis, systemic inflammatory response syndrome (SIRS), multiple organ dysfunction syndrome (MODS), graft-versus-host-disease (GVHD), traumatic injury, proinflammatory status in aged individuals, diabetes, atherosclerosis, neurodegenerative disease, autoimmune disease, eclampsia, infertility, coagulation disorder, pregnancy-associated complications and infection. Different subtypes of circulating cfDNA might play a significant role in progression of certain diseases and pathological conditions.

Plasma or serum is most commonly used to isolate cfDNA and detect cfDNA biomarkers. Recent metanalysis shows that methods of cfDNA isolation from plasma reported in the literature ranges from use of various in-house protocols to the use of commercially available kits. Of these, the QIAamp Circulating Nucleic Acid Kit (Qiagen) was most widely used (R. M. Trigg, L. J. Martinson, S. Parpart-Li, J. A. Shaw. Factors that influence quality and yield of circulating-free DNA: A systematic review of the methodology literature. Heliyon 4 (2018) e00699).

SUMMARY OF THE INVENTION

As specified in the Background section, above, there is a need for new and more sensitive, robust and versatile methods for detecting and analyzing cfDNA. The present invention addresses this and other needs.

In one aspect, the invention provides a method for isolating a cell free DNA (cfDNA) from a biological sample comprising the cfDNA, the method comprising:

(i) contacting the biological sample with a linker histone, wherein the linker histone forms a complex with the cfDNA;
(ii) separating the complex obtained in step (i) from the biological sample, and
(iii) releasing the cfDNA from the complex separated in step (ii).

In some embodiments, the method further comprises analyzing the released cfDNA. In one embodiment, the released cfDNA is analyzed to diagnose a disease. In another embodiment, the released cfDNA is analyzed to monitor a disease. In some embodiments, the method further comprises selecting a therapy for a disease.

In some embodiments, the linker histone is immobilized on a solid support.

In some embodiments, the linker histone is in a water-insoluble form.

In some embodiments, the linker histone is bound to a magnetic particle.

In some embodiments, the biological sample used in the method of the invention is a biofluid sample. Non-limiting examples of useful biofluid samples include, e.g., a serum sample, a plasma sample, a cerebrospinal fluid (CSF) sample, a lymph sample, an endometrial fluid sample, a urine sample, a saliva sample, a tear fluid sample, a synovial fluid sample, and a sputum sample. In some embodiments, the biofluid sample is selected from a blood sample, a plasma sample, and a serum sample. In one embodiment, the blood sample is a menstrual blood sample.

In some embodiments, the biological sample used in the method of the invention is a stool sample or a breath sample. In one embodiment, the breath sample is condensed breath (e.g., an extract of condensed breath, a purification of condensed breath, or a dilution of condensed breath).

In some embodiments, the biological sample used in the method of the invention is obtained from a patient.

In some embodiments, the linker histone is a mammalian somatic linker histone.

In some embodiments, the linker histone is a linker histone H1 or a linker histone H5. In some embodiments, the linker histone H1 is selected from an H1.0 linker histone, an H1.1 linker histone, an H1.2 linker histone, an H1.3 linker histone, an H1.4 linker histone, and an H1.5 linker histone. In one embodiment, the linker histone H1 is a human H1.3 linker histone. In another embodiment, the linker histone H1 is a human H1.0 linker histone.

In one embodiment, the linker histone comprises an amino acid sequence which is at least 70% identical (e.g., at least 80% identical, at least 85% identical, at least 90% identical, at least 95% identical, at least 98% identical, or at least 99% identical) to the sequence

```
                                        (SEQ ID NO: 1)
MSETAPLAPTIPAPAEKTPVKKKAKKAGATAGKRKASGPP

VSELITKAVAASKERSGVSLAALKKALAAAGYDVEKNNSR

IKLGLKSLVSKGTLVQTKGTGASGSFKLNKKAASGEGKPK

AKKAGAAKPRKPAGAAKKPKKVAGAATPKKSIKKTPKKVK
```

-continued

```
KPATAAGTKKVAKSAKKVKTPQPKKAAKSPAKAKAPKPKA

AKPKSGKPKVTKAKKAAPKKK.
```

In another embodiment, the linker histone comprises an amino acid sequence which is at least 70% identical (e.g., at least 80% identical, at least 85% identical, at least 90% identical, at least 95% identical, at least 98% identical, or at least 99% identical) to the sequence

```
                                          (SEQ ID NO: 2)
TENSTSAPAAKPKRAKASKKSTDHPKYSDMIVAAIQAEKN

RAGSSRQSIQKYIKSHYKVGENADSQIKLSIKRLVTTGV

LKQTKGVGASGSFRLAKSDEPKKSVAFKKTKKEIKKVATP

KKASKPKKAASKAPTKKPKATPVKKAKKKLAATPKKAKKP

KTVKAKPVKASKPKKAKPVKPKAKSSAKRAGKKK.
```

In yet another embodiment, the linker histone comprises an amino acid sequence which is at least 70% identical (e.g., at least 80% identical, at least 85% identical, at least 90% identical, at least 95% identical, at least 98% identical, or at least 99% identical) to the sequence

```
                                          (SEQ ID NO: 3)
TDSPIPAPAPAAKPKRARAPRKPASHPTYSEMIAAAIRAD

KSRGGSSRQSIQKYVKSHYKVGQHADLQIKLAIRRLLTTG

VLKQTKGVGASGSFRLAKGDKAKRSPAGRKKKKKAARKST

SPKKAARPRKARSPAKKPKAAARKARKKSRASPKKAKKPK

TVKAKSLKTSKPKKARRSKPRAKSGARKSPKKK.
```

In a further embodiment, the linker histone comprises an amino acid sequence which is at least 70% identical (e.g., at least 80% identical, at least 85% identical, at least 90% identical, at least 95% identical, at least 98% identical, or at least 99% identical) to the sequence

```
                                          (SEQ ID NO: 4)
MTESLVLSPAPAKPKRVKASRRSASHPTYSEMIAAAIRAE

KSRGGSSRQSIQKYIKSHYKVGHNADLQIKLSIRRLLAA

GVLKQTKGVGASGSFRLAKSDKAKRSPGKKKKAVRRSTSP

KKAARPRKARSPAKKPKATARKARKKSRASPKKAKKPKTV

KAKSRKASKAKKVKRSKPRAKSGARKSPKKK.
```

In some embodiments of the method of the invention, releasing the cfDNA comprises contacting the complex with a protease. In one embodiment, the protease is proteinase K.

In some embodiments of the method of the invention, releasing the cfDNA further comprises purifying the cfDNA by phenol-chloroform extraction or by extraction with phenol, chloroform, and isoamyl alcohol. In one embodiment, releasing the cfDNA comprises purifying the cfDNA by extraction with a 25:24:1 ratio of phenol, chloroform, and isoamyl alcohol.

In some embodiments of the method of the invention, releasing the cfDNA further comprises purifying the cfDNA by sodium iodine purification.

In some embodiments of the method of the invention, releasing the cfDNA further comprises purifying the cfDNA by isopropanol precipitation.

In some embodiments of the method of the invention, releasing the cfDNA further comprises purifying the cfDNA by ethanol precipitation.

In some embodiments of the method of the invention, the separating step (ii) comprises capturing the complex with an affinity matrix comprising an anti-histone antibody.

In some embodiments of the method of the invention, the separating step (ii) comprises capturing the complex with an affinity matrix comprising an anti-histone aptamer.

In some embodiments of the method of the invention, the separating step (ii) comprises capturing the complex with an affinity matrix comprising a linker histone-binding moiety.

In one embodiment of any of the above embodiments involving an affinity matrix, such affinity matrix is packed in a column.

In some embodiments of the method of the invention, the separating step (ii) comprises one or more of centrifugation, sedimentation or filtration.

In some embodiments of the method of the invention, the step of analyzing the released cfDNA comprises performing one or more of DNA sequencing (e.g., Sanger sequencing, targeted next-generation sequencing (NGS), whole-genome NGS, etc.), methylated DNA sequencing analysis, polymerase chain reaction (PCR) (e.g., multiplex digital PCR (dPCR), Intplex allele-specific PCR, co-amplification at lower denaturation temperature PCR (cold PCR), digital PCR such as, e.g., BEAMing, etc.), MIDI-Activated Pyrophosphorolysis (MAP), blot analysis, personalized analysis of rearranged ends (PARE), mass spectrometry, DNA quantification (e.g., quantitative or semiquantitave), and DNA electrophoresis. In one embodiment, the analyzing step comprises performing PCR-single strand conformation polymorphism analysis (PCR-SSCP) followed by direct sequencing.

In some embodiments of the method of the invention, the linker histone is bound to an affinity matrix. In some embodiments, the linker histone may be presented as its conjugate with a polymer (e.g., with a polypeptide, polysaccharide or with a non-biodegradable polymer). In some embodiments, the linker histone may be presented as its conjugate with a high-molecular weight organic carrier (e.g., a dendrimer) or with particle carrier (e.g., with nanoparticles such as, for example, magnetic nanoparticles [e.g., magnetic nanoparticles comprising a magnetic material (e.g., iron, nickel and cobalt) and a chemical or biochemical component that has functionality]).

In some embodiments of the method of the invention, the cfDNA is nucleosome-bound cfDNA and/or exosome-bound cfDNA, and/or unbound cfDNA. In some embodiments, the unbound cfDNA comprises dsDNA and/or ssDNA and/or oligonucleotides.

In a related aspect, the invention provides a method of treating a disease in a patient in need thereof, the method comprising isolating cfDNA from a biological sample obtained from the patient according to any of the above embodiments of the method of the invention, determining if the amount of isolated cfDNA is elevated in the patient sample as compared to a control (e.g., a predetermined value or the level of the cfDNA isolated from a healthy subject [e.g., subject matched by age and/or sex to the patient]), and administering a therapeutic compound or a treatment to the patient to treat the disease. In some embodiments, the therapeutic compound or treatment is administered to the patient only if the amount of isolated cfDNA in the patient sample is elevated as compared to the control. In some embodiments, the therapeutic compound or treatment reduces the level of the cfDNA in the patient. In some embodiments, the reduction of the level of cfDNA is performed by administering an enzyme having deoxyribonuclease (DNase) activity. Non-limiting examples of such enzymes having DNase activity include, e.g., DNase I, DNase X, DNase γ, DNase 1L1, DNase 1L2, DNase 1L3, DNase II, DNase IIα, DNase 11β, Caspase-activated DNase (CAD), Endonuclease G (ENDOG), Granzyme B (GZMB), phosphodiesterase I, lactoferrin, acetylcholinesterase, or mutants or derivatives thereof. In one embodiment, wherein the cfDNA is present in the blood, the reduction of the level of the cfDNA is performed by an apheresis procedure. Non-limiting examples of the diseases treatable by the method of the invention include, e.g., neurodegenerative diseases, cancers, chemotherapy-related toxicities, irradiation induced toxicities, organ failures, organ injuries, organ infarcts, ischemia, acute vascular events, a stroke, graft-versus-host-disease (GVHD), graft rejections, sepsis, systemic inflammatory response syndrome (SIRS), cytokine releasing syndrome (CRS), multiple organ dysfunction syndrome (MODS), traumatic injuries, aging, diabetes, atherosclerosis, autoimmune disorders, eclampsia, preeclampsia, infertility, pregnancy-associated complications, coagulation disorders, asphyxia, drug intoxication, poisoning, and infections. In one specific embodiment, the disease is a cancer.

In some embodiments of the methods of the invention, the patient is human.

These and other aspects and embodiments of the present invention will be apparent to those of ordinary skill in the art in the following description and claims.

DETAILED DESCRIPTION OF THE INVENTION

Definitions

Unless defined otherwise, all technical and scientific terms used herein have the same meaning as commonly understood by one of ordinary skill in the art to which this invention belongs.

Singular forms "a", "an", and "the" include plural references unless the context clearly dictates otherwise. Thus, for example, a reference to "a method" includes one or more methods, and/or steps of the type described herein and/or which will become apparent to those persons skilled in the art upon reading this disclosure.

The term "about" or "approximately" includes being within a statistically meaningful range of a value. Such a range can be within an order of magnitude, preferably within 50%, more preferably within 20%, still more preferably within 10%, and even more preferably within 5% of a given value or range. The allowable variation encompassed by the term "about" or "approximately" depends on the particular system under study, and can be readily appreciated by one of ordinary skill in the art.

The term "device" as used herein refers to any assembly known in the art to enable the purification of liquid solutions, such as, without limitation, e.g., any hollow-ware, a column, a column matrix, a filter, a membrane, a semi-permeable material, a bead (e.g., a microbead or a nano-bead), or a tubing. The terms "column" and "cartridge" are used interchangeably herein in the context of an apheresis device.

The term "affinity matrix" as used herein refers to (i) a solid support into which linker histone is immobilized or to (ii) a solid support formed by the ligand itself (e.g., a water-insoluble form, e.g., oligomer, polymer or co-polymer comprising any of the linker histone molecules described herein). The term "DNA-binding protein" refers to proteins that bind to single-stranded DNA (ssDNA) or double-stranded DNA (dsDNA). DNA binding proteins can bind DNA in sequence-specific manner (e.g., transcription factors and nucleases) or non-sequence specifically (e.g., polymerases and histones). The linker histone family members are key components of chromatin and bind to the nucleosomal core particle around the DNA entry and exit sites.

As used herein, the terms "circulating DNA", "circulating cell free DNA (cfDNA)", and "circulating extracellular DNA (eDNA)" are used interchangeably to refer to DNA present in blood or plasma located outside of circulating cells of hematopoietic and non-hematopoietic origin. As used herein, the terms "cell free DNA (cfDNA)", "extracellular DNA (eDNA)", are used interchangeably to refer to DNA present in a biofluid located outside of cells.

Nucleosome-bound cfDNA is DNA that is bound to a nucleosome. A nucleosome is a subunit of nuclear chromatin. Nucleosome-bound cfDNA might circulate in blood as mononucleosomes or higher order structures such as oligonucleososmes or even fragments of chromatin containing over $50\text{-}100\times10^3$ base pairs of DNA. Circulating nucleosome-bound cfDNA may originate from cells undergoing necrosis or apoptosis and from neutrophil NETosis.

Exosome-bound cfDNA is cfDNA that is bound to exosomes or present in exosomes. Exosomes are small membrane vesicles (about 30-100 nm) of exocytotic origin secreted by most cell types that might contain single-stranded DNA (ssDNA), mitochondrial DNA (mtDNA) and double-stranded DNA (dsDNA) at the inner or outer space of exosome.

The terms "unbound cfDNA" or "cfDNA free of particles" or "particle free cfDNA" refer to cfDNA which is not bound to exosomes or nucleosomes and encompasses double-stranded DNA (dsDNA), single-stranded DNA (ssDNA), linear or circular and oligonucleotides, including ultrashort DNA molecules of subnucleosomal size (usually less than 147 base pairs).

The term "linker histone" is used herein to refer to the primary protein components of chromatin which bind to the nucleosome core particle at the linker (internucleosomal) DNA entry and exit points, provide an interaction region between adjacent nucleosomes and generate second-order chromatin structure (i.e., nucleosomal filament) by drawing adjacent nucleosomes together. Linker histones typically (but not always) possess a tripartite structure conserved across all eukaryotes, including a short and flexible N-terminal tail, a structured globular domain (GH1) which interacts with a nucleosome dyad, and a structurally disordered, lysine-rich C-terminal tail. The C-terminal tails vary in length and composition among linker histone isotypes and organisms. The linker histones H1 and H5 are the most divergent group of the histone proteins. Histone H1 protein family comprises 12 subtypes. The individual subtypes can be grouped into 3 distinct groups: (i) the somatic replication-dependent subtypes (H1.1-H1.5) that are expressed mainly in the S-phase, (ii) the somatic replication-independent variants (H1.0 and H1.10) expressed during the complete cell cycle and (iii) the germ line-specific (testis or oocyte) subtypes (H1.6 (TS), H1.7 (TS), two splice variants of H1.8 (00) and H1.9 (TS)). See, e.g., Brockers, K., Schneider, R., Epigenomics, 2019, 11(4):363-366; doi: 10.2217/epi-2019-0018; Hergeth, S. P., Schneider, R., EMBO Rep., 2015; 16(11):1439-1453. doi:10.15252/embr.201540749. A specific subtype of linker histones, histone H5, has been found to accumulate in nucleated avian erythrocytes. Histone H5 is a counterpart of mammalian histone H1.0 and both of them are considered to be differentiation-specific histone subvariants (Gunj an, A, et al., J Biol Chem. 1999; 274(53):37950-6; Smith B J, et al., FEBS Lett., 1980; 112(1):42-44; Koorsen, G (2010) "The binding of linker histone H5 to DNA and chromatin" VDM publishing, ISBN3639222105).

As used herein, the terms "subject" and "patient" are used interchangeably and refer to animals, including mammals such as humans, veterinary animals (e.g., cats, dogs, cows, horses, sheep, pigs, etc.), and experimental animal models. In certain embodiments, the subject refers to a human patient, including both genders in adult and child populations.

By "sequence identity" is intended the same amino acid residues are found within the variant sequence and a reference sequence when a specified, contiguous segment of the nucleotide sequence or amino acid sequence of the variant is aligned and compared to the nucleotide sequence or amino acid sequence of the reference sequence. Methods for sequence alignment and for determining identity between sequences are well known in the art. See, for example, Ausubel et al., eds. (1995) Current Protocols in Molecular Biology, Chapter 19 (Greene Publishing and Wiley-Interscience, New York); and the ALIGN program (Dayhoff (1978) in Atlas of Polypeptide Sequence and Structure 5: Suppl. 3 (National Biomedical Research Foundation, Washington, D.C.).

In the context of the present invention, the term "liquid biopsy" refer to broad category for a minimally invasive test done for a sample of a biofluid (e.g., blood, blood plasma or blood serum) to look for fragments of tumor derived DNA that are in the blood. Tumor genetics or genomics from tumor derived DNA assays are one example. See, for example, Merker at al., (2018) Circulating Tumor DNA Analysis in Patients With Cancer: American Society of Clinical Oncology and College of American Pathologists Joint Review, Journal of Clinical Oncology 36(16): JCO2017768671, DOI: 10.1200/JCO.2017.76.8671.

In the context of the present invention insofar as it relates to any of the disease conditions recited herein, the terms "treat", "treatment", and the like mean to relieve or alleviate at least one symptom associated with such condition, or to slow or reverse the progression of such condition. Within the meaning of the present invention, the term "treat" also denotes to arrest, delay the onset (i.e., the period prior to clinical manifestation of a disease) and/or reduce the risk of developing or worsening a disease. The terms "treat", "treatment", and the like regarding a state, disorder or condition may also include (1) preventing or delaying the appearance of at least one clinical or sub-clinical symptom of the state, disorder or condition developing in a subject that may be afflicted with or predisposed to the state, disorder or condition but does not yet experience or display clinical or subclinical symptoms of the state, disorder or condition; or (2) inhibiting the state, disorder or condition, i.e., arresting, reducing or delaying the development of the disease or a relapse thereof (in case of maintenance treatment) or at least one clinical or sub-clinical symptom thereof; or (3) relieving the disease, i.e., causing regression of the state, disorder or condition or at least one of its clinical or sub-clinical symptoms.

The practice of the present invention employs, unless otherwise indicated, conventional techniques of statistical analysis, molecular biology (including recombinant techniques), microbiology, cell biology, conjugation chemistry and biochemistry, which are within the skill of the art. Such tools and techniques are described in detail in e.g., Sambrook et al. (2001) Molecular Cloning: A Laboratory Manual. 3rd ed. Cold Spring Harbor Laboratory Press: Cold Spring Harbor, New York; Ausubel et al. eds. (2005) Current Protocols in Molecular Biology. John Wiley and Sons, Inc.: Hoboken, NJ; Bonifacino et al. eds. (2005) Current Protocols in Cell Biology. John Wiley and Sons, Inc.: Hoboken, NJ; Coligan et al. eds. (2005) Current Protocols in Immunology, John Wiley and Sons, Inc.: Hoboken, NJ; Coico et al. eds. (2005) Current Protocols in Microbiology, John Wiley and Sons, Inc.: Hoboken, NJ; Coligan et al. eds. (2005) Current Protocols in Protein Science, John Wiley and Sons, Inc.: Hoboken, NJ; and Enna et al. eds. (2005) Current Protocols in Pharmacology, John Wiley and Sons, Inc.: Hoboken, NJ. Hermanson (2013) Bioconjugate Techniques, 3rd ed., Academic Press; Niemeyer (2004) Bioconjugation Protocols: Strategies and Methods, Springer Science & Business Media and Hermanson et al. (1992) Immobilized Affinity Ligand Techniques, Academic Press. Additional techniques are explained, e.g., in U.S. Pat. No. 7,912,698 and U.S. Patent Appl. Pub. Nos. 2011/0202322 and 2011/0307437.

Devices and Methods of the Invention

As specified in the Background Section, there is a need for a more robust and versatile method for enriching or purifying cfDNA, for improved methods of detecting blood cfDNA and for new more effective devices to realize such methods. The present disclosure addresses this and other needs by providing devices and methods for isolation and analyzing of cfDNA from a biofluid sample, including nucleosome-bound cfDNA, exosome-bound cfDNA and unbound cfDNA (including dsDNA, ssDNA and oligonucleotides).

The present disclosure provides a method for isolation of cfDNA, and for treating diseases characterized by elevated circulating levels of cfDNA through the removal of substantially all types of cfDNA, including nucleosome-bound cfDNA, exosome-bound cfDNA and unbound cfDNA (including dsDNA, ssDNA and oligonucleotides) from the blood of a subject to reduce the negative effects of the circulating cfDNA. The method of isolating cfDNA may be combined with various methods for detecting and analyzing cfDNA.

Without wishing to be bound by theory, in certain diseases, wherein the level of circulating cfDNA is increased, different types of circulating cfDNA might act in concert by triggering different molecular pathways each leading to disease progression and patient mortality; different types of circulating cfDNA acting together might generate synergistic toxicity, i.e., toxic (negative) effect of two or more types of circulating cfDNA is greater than the sum of the negative effects of each type of cfDNA taken separately.

It is further described herein that affinity matrices or combinations thereof are able to effectively capture substantially all types of cfDNA, including nucleosome-bound cfDNA, exosome-bound cfDNA and unbound cfDNA (including dsDNA, ssDNA and oligonucleotides) from the blood of patients in need thereof. Examples of affinity matrices useful in devices and methods of the invention include matrices comprising a DNA binding protein (e.g., a linker histone [e.g., a linker histone H1 or a linker histone H5]).

In one aspect, the invention provides a method for isolating a cell free DNA (cfDNA) from a biological sample comprising the cfDNA, the method comprising:

(i) contacting the biological sample with a linker histone, wherein the linker histone forms a complex with the cfDNA;

(ii) separation of the complex obtained in step (i), and (iii) releasing the cfDNA from the complex separated in step (ii).

In another aspect is provided a method for isolating a cell free DNA (cfDNA) from a biological sample comprising the cfDNA, the method comprising:

(i) contacting the biological sample with a linker histone, wherein the linker histone forms a complex with the cfDNA;

(ii) separating the complex obtained in step (i) from the biological sample, and (iii) releasing the cfDNA from the complex separated in step (ii).

cfDNA can include small DNA fragments in the range of 140-170 base pairs (bp). The amount and state of cells in the body associated with disease (e.g., cancer cells or immunopathological conditions, for example, SIRS or sepsis) can influence the overall amount of cfDNA. In addition, the presence and state of such cells (e.g., in cancer, the tumor type, progression, burden, proliferation rates, and therapy or e.g., in sepsis, sepsis stage, deep of organ-failures, and therapy) can affect the quantity and quality (e.g. methylation pattern, size of DNA fragments, fragment size distribution pattern) of cfDNA in a sample. These factors can also affect the amount of specific cfDNAs, for example, nucleosome DNA, or unbound DNA, or exosomal DNA, or tumor derived cfDNA (ctDNA), or NET-derived DNA in a sample. An improved analysis of the disease state of a patient can be obtained by isolating and quantifying individual cfDNA known to be associated with diseases. Isolated cfDNA may be analyzed for quantification of a specific gene (for example, mutant tumor cells-derived gene) or detection of other circulating genomic aberrations.

Thus, analysis of cfDNA identifies mutations arising in, and the pathognomonicity of, tumor DNA. The analysis of biofluids (including blood plasma) broadly used for early cancer diagnosis, monitoring of anti-tumor therapy efficacy, prognosis and selection of the type of therapy. For example, patients with mutant EGFR-driven lung adenocarcinoma receiving EGFR tyrosine kinase inhibitor (TKI) therapy (such as osimertinib, rociletinib, HM61713/BI1482694, ASP8273, and EGF816, which specifically target EGFR T790M) had better response rates and progression-free survival (PFS) when compared to those receiving traditional standard chemotherapy. To guide the treatment options (TKI or other therapy) this analysis of cfDNA should be performed correctly; the amount and quality of isolated cfDNA play pivotal role in this case. See, e.g., Su K Y, Tseng J S, Liao K M, et al. Mutational monitoring of EGFR T790M in cfDNA for clinical outcome prediction in EGFR-mutant lung adenocarcinoma. PLoS One. 2018; 13(11):e0207001; doi:10.1371/journal.pone.0207001.

Without wishing to be bound by theory, the use of linker histone molecules as described herein to purify cfDNA provides advantages over existing methods of purifying cfDNA, particularly those involving use of silica. The most prominent problem of the known silica-based methods is that only some fragments or types of cfDNA are isolated. For example, only small-sized cfDNA fragments, or even only large sized cfDNA fragments are isolated. Such undesired "selective" isolation may lead to an underestimation of 1) the total quantity of cfDNA, and/or 2) the concentration (copy/mL) of mutant genes or other genes of interest in the biofluids. The methods described herein provided for substantially less selective isolation. The methods described herein may provide for an increased total quantity of cfDNA as compared with silica-based methods. The total quantity of cfDNA can be at least 10%, at least 15%, at least 20%, at least 25%, at least 30%, at least 35%, or at least 40%, as compared to a silica-based method. The concentration of cfDNA can be at least 50%, at least 75%, at least 100%, at least 125%, at least 150%, at least 175%, at least 200%, at least 225%, at least 250%, at least 275%, at least 300%, at least 325%, at least 350%, at least 375%, at least 400%, at least 450%, at least 500%, at least 550%, or at least 600%, as compared to a silica-based method.

Various linker histone proteins may be used to isolate cfDNA from the biological sample. Without wishing to be bound by theory, the most basic structural unit of the chromatin is a nucleosome formed by the binding of DNA to histone octamers containing two monomers for each of the four core histones form the basic structural unit of chromatin. Nucleosomes are separated from each other by the linker stretches of nucleotides that are generally up to 80 base pairs long. Linker histone proteins can bind to these linker stretches. In some embodiments, the linker histone is a mammalian somatic linker histone. In certain embodiments, the linker histone H1 is selected from an H1.0 linker histone, H1.1 linker histone, an H1.2 linker histone, an H1.3 linker histone, an H1.4 linker histone, and an H1.5 linker histone. In a specific embodiment, the linker histone H1 is presented as one of extreme variants, namely H5 linker histone. In a specific embodiment, the linker histone H1 is a human H1.3 linker histone. In one specific embodiment, the linker histone comprises an amino acid sequence which is at least 70% identical (e.g., at least 80% identical, at least 85% identical, at least 90% identical, at least 95% identical, at least 98% identical, at least 99% identical) to the sequence of human H1.3 linker histone

```
                                       (SEQ ID NO: 1)
MSETAPLAPTIPAPAEKTPVKKKAKKAGATAGKRKASGPP

VSELITKAVAASKERSGVSLAALKKALAAAGYDVEKNNSR

IKLGLKSLVSKGTLVQTKGTGASGSFKLNKKAASGEGKPK

AKKAGAAKPRKPAGAAKKPKKVAGAATPKKSIKKTPKKVK

KPATAAGTKKVAKSAKKVKTPQPKKAAKSPAKAKAPKPKA

AKPKSGKPKVTKAKKAAPKKK.
```

In another specific embodiment, the linker histone comprises an amino acid sequence which is at least 70% identical (e.g., at least 80% identical, at least 85% identical, at least 90% identical, at least 95% identical, at least 98% identical, at least 99% identical) to the sequence of the human H1.0 linker histone TENSTSAPAAKPKRAKASKKSTDHPKYSDMIVAAIQAEKNRAGSSRQSIQKYIKSHYKV GENADSQIKLSIKRLVTTGVLKQTKGVGASGSFRLAKSDEPKKSVAFKKTKKEIKKVAT PKKASKPKKAASKAPTKKPKATPVKKAKKKLAATPKKAKKPKTVKAKPVKASKPKKA KPVKPKAKSSAKRAGKKK (SEQ ID NO: 2). In yet another specific embodiment, the linker histone comprises an amino acid sequence which is at least 70% identical (e.g., at least 80% identical, at least 85% identical, at least 90% identical, at least 95% identical, at least 98% identical, at least 99% identical) to the sequence of histone H5 of Anser anser (Western greylag goose), UniProt P02258 TDSPIPA- PAPAAKPKRARAPRKPASHPTYSEMIAAAIRAD-KSRGGSSRQSIQKYVKSHYK VGQHADLQIKLAI-RRLLTTGVLKQTKGVGASGSFRLAKGDKAKR-SPAGRKKKKKAARK STSPKKAARPRKARSPAKKP-KAAARKARKKSRASPKKAKKPKTVKAKSLKTSKPK-KAR RSKPRAKSGARKSPKKK (SEQ ID NO: 3). In a further specific embodiment, the linker histone comprises an amino acid sequence which is at least 70% identical (e.g., at least 80% identical, at least 85% identical, at least 90% identical, at least 95% identical, at least 98% identical, at least 99% identical) to the sequence of histone H5 of *Gallus gallus*, UniProt P02259

```
                                        (SEQ ID NO: 4)
MTESLVLSPAPAKPKRVKASRRSASHPTYSEMIAAAIRAE

KSRGGSSRQSIQKYIKSHYKVGHNADLQIKLSIRRLLAAG

VLKQTKGVGASGSFRLAKSDKAKRSPGKKKKAVRRSTSPK

KAARPRKARSPAKKPKATARKARKKSRASPKKAKKPKTVK

AKSRKASKAKKVKRSKPRAKSGARKSPKKK.
```

In some embodiments, the linker histone is immobilized on a solid support. In some embodiments, the linker histone forms a solid support by the itself (e.g., a water-insoluble form of liker histone, e.g., an oligomer, polymer or co-polymer comprising any of the linker histone molecules described herein).

In some embodiments, the linker histone may be presented as its conjugate with a polymer (e.g., with a polypeptide, polysaccharide or with a non-biodegradable polymer). The polymer may be a cationic polymer, e.g., poly (ethylenimine), poly(amidoamine) (PAMAM), poly (aspartamide), polypeptoids (e.g., for forming "spiderweb"-like branches for core condensation), a charge-functionalized polyester, a cationic polysaccharide, an acetylated amino sugar, chitosan, or a cationic polymer that comprises any combination thereof (e.g., in linear or branched forms). The cationic polymer may be covalently associated with a linker histone. The nanoparticle may also comprise a cationic polymer composition that comprises a linker histone and another cationic polymer (such as those described above).

In some embodiments, the linker histone may be presented as its conjugate with a high-molecular weight organic carrier (e.g., a dendrimer) or with particle carrier (e.g., with nanoparticles such as, for example, magnetic nanoparticles [which, in some embodiments, may consist of two components, a magnetic material, often iron, nickel and cobalt, and a chemical or biochemical component that has functionality]).

In certain embodiments, the linker histone is conjugated to a dendrimer. The dendrimer may be a polyamidoamine (PAMAM) dendrimer, such as that described in International Patent Publication No. WO2019/053243, incorporated by reference herein in its entirety. The linker histone may be conjugated to a polyamidoamine (PAMAM) dendrimer affinity matrix (PDAM) or polypropyleneimine (PPI) dendrimer affinity matrix. See, e.g., Kaur et al., J Nanopart Res., 2016, 18: 146. Dendrimers are unique synthetic polymers of nanometer dimensions with a highly branched structure and globular shape. Among dendrimers, polyamidoamine (PAMAM) have received most attention as potential transfection agents for gene delivery, because these macro molecules bind DNA at physiological pH. PAMAM dendrimers consist of an alkyl-diamine core and tertiary amine branches. They are available in ten generations with 5 different core types and 10 functional surface groups. DNA and polyamidamine (PAMAM) dendrimers form complexes on the basis of the electrostatic interactions between negatively charged phosphate groups of the nucleic acid and protonated (positively charged) amino groups of the polymers. Formation of high molecular weight and high-density complexes depend mainly on the DNA concentration, with enhancement by increasing the dendrimer-DNA charge ratio. (Shcharbin, D. et al., Practical Guide to Studying Dendrimers. Book, iSmithers Rapra Publishing: Shawbury, Shrewsbury, Shropshire, U K, 2010. 120 p. ISBN: 978-1-84735-444-0.)

In certain embodiments, the linker histone is conjugated to a nanoparticle. The nanoparticles may be a phosphoramidite nanoparticle. In some embodiments, the nanoparticle is magnetic. The magnetic nanoparticle may comprise a single magnetic core and an outer shell, wherein the outer shell covers the magnetic core. The magnetic particle may comprise a metal oxide, e.g., $Fe_3O_4$. In some embodiments, the magnetic particle has a maximum diameter of 100 nm to 1000 nm. In some embodiments, the magnetic particle has a maximum diameter of 300 nm to 700 nm. In some embodiments, the magnetic particle has a maximum diameter of 400 nm to 600 nm.

In some embodiments, the nanoparticle has a maximum diameter of less than 1 μm, such as less than 900 nm, less than 800 nm, less than 700 nm, less than 600 nm, less than 500 nm, less than 400 nm, less than 300 nm, or less than 200 nm. In various embodiments, the magnetic nanoparticle has a maximum diameter of 100 nm to 1000 nm, such as 100 nm to 900 nm, 100 nm to 800 nm, 100 nm to 700 nm, 100 nm to 600 nm, 100 nm to 500 nm, 100 nm to 400 nm, 100 nm to 300 nm, 100 nm to 200 nm, 200 nm to 1000 nm, 200 nm to 900 nm, 200 nm to 800 nm, 200 nm to 700 nm, 200 nm to 600 nm, 200 nm to 500 nm, 200 nm to 400 nm, 200 nm to 300 nm, 300 nm to 1000 nm, 300 nm to 900 nm, 300 nm to 800 nm, 300 nm to 700 nm, 300 nm to 600 nm, 300 nm to 500 nm, 300 nm to 400 nm, 400 nm to 1000 nm, 400 nm to 900 nm, 400 nm to 800 nm, 400 nm to 700 nm, 400 nm to 600 nm, 400 nm to 500 nm, 500 nm to 1000 nm, 500 nm to 900 nm, 500 nm to 800 nm, 500 nm to 700 nm, 500 nm to 600 nm, 600 nm to 1000 nm, 600 nm to 900 nm, 600 nm to 800 nm, 600 nm to 700 nm, 700 nm to 1000 nm, 700 nm to 900 nm, 700 nm to 800 nm, 800 nm to 1000 nm, 800 nm to 900 nm, or 900 nm to 1000 nm. In certain embodiments, the magnetic core has a maximum diameter of about 900 nm. In certain embodiments, the magnetic core has a maximum diameter of about 800 nm. In certain embodiments, the magnetic core has a maximum diameter of about 700 nm. In certain embodiments, the magnetic core has a maximum diameter of about 600 nm. In certain embodiments, the magnetic core has a maximum diameter of about 500 nm. In certain embodiments, the magnetic core has a maximum diameter of about 400 nm. In certain embodiments, the magnetic core has a maximum diameter of about 300 nm. In certain embodiments, the magnetic core has a maximum diameter of about 200 nm.

In some embodiments, the nanoparticle comprises a cationic polymer, e.g., poly(ethylenimine), poly(amidoamine) (PAMAM), poly(aspartamide), polypeptoids (e.g., for forming "spiderweb"-like branches for core condensation), a charge-functionalized polyester, a cationic polysaccharide, an acetylated amino sugar, chitosan, or a cationic polymer that comprises any combination thereof (e.g., in linear or branched forms). The cationic polymer may be covalently associated with a linker histone. The nanoparticle may also comprise a cationic polymer composition that comprises a linker histone and another cationic polymer (such as those described above).

In another aspect is provided a method of performing a liquid biopsy for diagnosis of cancer in a subject, the method comprising:

(i) contacting a blood sample, a plasma sample, or a serum sample from the subject with a linker histone, wherein the sample comprises a cfDNA, and wherein the linker histone forms a complex with the cfDNA;
(ii) separating the complex obtained in step (i)
(iii) releasing the cfDNA from the complex separated in step (ii); and
(iv) analyzing the released cfDNA.

In another aspect is provided a method of performing a liquid biopsy for monitoring a cancer in a subject, the method comprising:

(i) contacting a sample with a linker histone, wherein the sample comprises a cfDNA, wherein the sample is a biofluid sample, a plasma sample, or a serum sample, and wherein the linker histone forms a complex with the cfDNA;
(ii) separating the complex obtained in step (i);
(iii) releasing the cfDNA from the complex separated in step (ii); and
(iv) analyzing the released cfDNA.

In another aspect is provided a method of performing a liquid biopsy for selection of therapy of a cancer in a subject, the method comprising:

(i) contacting a biofluid sample (e.g., a blood sample, a plasma sample, or a serum sample) from the subject with a linker histone, wherein the sample comprises a cfDNA, and wherein the linker histone forms a complex with the cfDNA;
(ii) separating the complex obtained in step (i)
(iii) releasing the cfDNA from the complex separated in step (ii); and
(iv) analyzing the released cfDNA.

In various embodiments of the above, the linker histone is conjugated to a matrix or to beads. The matrix or beads can be spun down or isolated so as to enrich for the linker histone. In certain embodiments, the matrix is a cellulose matrix. In certain embodiments, the matrix is a magnetic bead. In some embodiments, the linker histone is bound to an affinity matrix.

The affinity column may comprise a histone affinity matrix. In one embodiment, the histone affinity matrix may comprise recombinant human histone H1.3. The histone affinity matrix may be part of an affinity column. The beads used as support in a histone affinity matrix column may be cellulose beads that are oxidized with an oxidant before coupling with histone. The beads can be sepharose beads, for example. Alternatively, support of forms besides beads can be used (hollow fiber, membrane, tubing, etc.). Support of affinity matrix may be made from other organic and inorganic compounds known to one of skill in the art, for example, polyvinylpyrrolidone (PVP), polysulfone (PS), polyethersulfone (PES), polyarylethersulfone (PAES), polyacrylate, poly(methyl methacrylate) (PMMA), poly(glycidyl methacrylate) (PGMA), poly(hydroxy metacrylate), polystyrene (PS), polytetrafluoroethylene (PTFE), polyacrylamide, polyacrolein, acrylonitrile butadiene styrene (ABS), polyacrylonitrile (PAN), polyurethane (PU), Eupergit®, polyethylene glycol (PEG), hyperfluorocarbon, agarose (i.e. cross-linked agarose), alginate, carrageenan, chitin, starch, cellulose, nitrocellulose, sepharoseg, glass, silica, kieselguhr, zirconia, alumina, iron oxide, porous carbon and mixtures and/or derivatives of said solid supports; and protonated and deprotonated forms of this separation material.

The linker histone may be immobilized by chemically coupling it to a solid insoluble support matrix such as polysaccharide beads. For example, agarose beads can be activated using cyanogen bromide and the linker histone can be incubated with the activated agarose to allow coupling to occur. The unconjugated material can be removed by washing with buffer and the protein bound agarose is packed into the targeted affinity cartridge. There are many different methods of chemically coupling proteins to a variety of insoluble support matrixes. These and other matrix materials and methods of protein coupling known to those skilled in the art may be used in any of the methods and devices described herein.

For example, the attachment of a linker histone to a solid support can be through an amine, a thiol, an imide (e.g., a water-soluble carbodiimide), or other chemical attachment method known to one of skill in the art to attach a polypeptide or oligonucleotide to a solid support.

The size of the beads can range from 30 to 200 microns, 40 to 180 microns, 45 to 165 microns, 60 to 150 microns, for example. Any number of oxidants may be used, such as sodium metaperiodate (NaIO). Alternatively, the primary hydroxyl group of cellulose can be selectively converted to yield 6-deoxy-6-carboxy-cellulose via oxidation mediated by piperidine oxoammonium salts (TEMPO) or oxidized with chlorite. See, for example, Eyle, S. and Thielemans, W., Surface modification of cellulose nanocrystals, Nanoscale, 2014, 6, 7764, DOI: 10.1039/c4nr01756k). Also, cellulose (or agarose) support can be oxidized by other compounds known to one of skill in the art, for example, chromic acid, chromium trioxide-pyridine, dimethylsulfoxide (see, for example, Peng, L. et al. Evaluation of activation methods with cellulose beads for immunosorbent purification of immunoglobulins, J. Biotechnology, 5 (1987) 255-265). The oxidized beads can be then incubated with a sufficiently purified and concentrated solution of a linker histone protein (e.g., recombinant human histone H1.3). The reaction may be stopped and then washed with buffer to remove soluble protein contaminants. Alternatively, the primary hydroxyl group of cellulose can be selectively converted to yield 6-deoxy-6-carboxy-cellulose via oxidation mediated by piperidine oxoammonium salts (TEMPO) or oxidized with chlorite. See, for example, Eyle, S. and Thielemans, W., Surface modification of cellulose nanocrystals, Nanoscale, 2014, 6, 7764, DOI: 10.1039/c4nr01756k. Also, cellulose (or agarose) support can be oxidized by other compounds known to one of skill in the art, for example, chromic acid, chromium trioxide-pyridine, dimethylsulfoxide. See, for example, Peng, L. et al. Evaluation of activation methods with cellulose beads for immunosorbent purification of immunoglobulins, J. Biotechnology, 5 (1987) 255-265.

The affinity column may comprise a linker histone affinity matrix. In one embodiment, the histone affinity matrix may comprise recombinant human histone H1.3. The linker histone affinity matrix may be part of an affinity column. The beads used in a linker histone affinity matrix column may be cellulose beads that are oxidized with an oxidant. The beads can be sepharose beads, for example. The beads may be coated with streptavidin. The size of the beads can range from 30 to 200 microns, 40 to 180 microns, 45 to 165 microns, 60 to 150 microns, for example. Any number of oxidants may be used, such as, e.g., sodium metaperiodate (NaIO). Alternatively, the primary hydroxyl group of cellulose can be selectively converted to yield 6-deoxy-6-carboxy-cellulose via oxidation mediated by piperidine oxoammonium salts (TEMPO). See, for example, Eyle, S. and Thielemans, W., Surface modification of cellulose nanocrystals, Nanoscale, 2014, 6, 7764, DOI: 10.1039/c4nr01756k). Also, cellulose (or agarose) support can be oxidized by other compounds known to one of skill in the art, for example: chromic acid, chromium trioxide-pyridine, dimethylsulfoxide. See, e.g., Peng, L. et al. Evaluation of activation methods with cellulose beads for immunosorbent purification of immunoglobulins, J. Biotechnology, 1987, 5:255-265. The oxidized beads can be then incubated with a sufficiently purified and concentrated solution of a linker histone protein (e.g., recombinant human histone H1.3). The reaction may be stopped and then washed with buffer to remove soluble protein contaminants.

In various embodiments, the histone affinity matrix is prepared by a process comprising a) oxidizing cellulose beads having a size between 100 and 250 micrometers to yield activated cellulose beads;
b) washing the activated cellulose beads;
c) preparing a concentrated solution of a linker histone;
d) incubating the activated cellulose beads with the concentrated solution of the linker histone; and
e) blocking any free CHO groups on the activated cellulose beads.

In a specific embodiment, the linker histone is recombinant human histone H1.3.

The above process may further comprise: f) washing the activated cellulose beads with buffer.

Any oxidant may be used in step a). One exemplary oxidant is NaIO. Any manner of washing can be undertaken in step b). For example, the activated cellulose beads may be washed with sodium bicarbonate, hydrochloric acid and water. Dialysis or other methods may be used in step c). For example, a solution of a linker histone (e.g., recombinant human histone H1.3) may be dialyzed and the dialyzed solution may be concentrated in 0.1 M $NaHCO_3$ at pH 7-9, or at pH 8. In step d), the incubation may be performed for 3-5 hours at 15-30° C., or for 4 hours at room temperature. In step e), the blocking step may comprise adding 1 M ethanolamine to the activated cellulose beads and reacting for 30 minutes to 2 hours at 15-30° C. In step f), the activated cellulose beads may be washed with TBS buffer.

The beads may be loaded onto a column, such as, e.g., a polytetraflouroethylene (PTFE) column. Other exemplary columns may have a wall made of polycarbonate, polyethylene, polyvinylchloride, polypropylene, polyethersulfone, polyester, or other polymer material approved by FDA or EMEA for manufacturing of devices for extracorporeal treatment of blood or a blood component.

The column, or cartridge device, can be also made of material that is nontoxic and which provides rigid support to the affinity matrix within. Typically, the material will be a plastic composition such as polycarbonate, polyethylene, polyvinylchloride, polypropylene, polyethersulfone, polyester, polystyrene, or other similar material approved by the regulators such as FDA or EMEA for manufacturing of devices for extracorporeal treating of blood or blood component. In some embodiments, there is an inside filter at the bottom of the column (cartridge) to prevent the affinity matrix from leaving the device. In some embodiments, there is also an inside filter at the top of the device to contain the affinity matrix within the device. In some embodiments, these filters are composed of plastic and/or cellulosic material and have pores that will allow through passage of fluid such as plasma, but not particulate material such as affinity matrix.

In preparing a linker histone affinity matrix column, the linker histone affinity matrix may be loaded to at least 50%, 60%, 70%, 75%, 80%, 85%, or 90% column volume. PBS, particularly cold PBS may be used to equilibrate the column. Other suitable buffers may also be used to equilibrate the column.

Affinity matrices may be placed into various affinity columns, chromatography columns, or cartridges. The affinity device can comprise a filtration cartridge and one or more affinity columns having an inlet and an outlet, in which the device is capable of capturing nucleosome-bound cfDNA, exosome-bound cfDNA and unbound cfDNA (including dsDNA, ssDNA and oligonucleotides), from blood or plasma of a patient. Preferably, the geometry of the device is designed to maximize contact of a biofluid with the affinity matrices during passage through the device. A variety of such designs are known in the art. For example, the device can be a hollow cylinder packed with an affinity ligand immobilized on beads, having the inlet at one end and the outlet at the opposite end. Other devices, such as microtubule arrays, can be also constructed. All such variations of container geometry and volume and of the affinity matrices contained therein can be designed according to known principles. In preparing an affinity matrix column, the affinity matrix may be loaded to at least 50%, 60%, 70%, 75%, 80%, 85%, or 90% column volume. A suitable buffer (e.g., PBS, particularly cold PBS) may be used to equilibrate the column.

In one embodiment, the linker histone affinity matrix comprises cellulose beads and recombinant human histone H1.3, wherein the recombinant human histone H1.3 is immobilized on the cellulose beads and wherein the size of the beads is between 50 and 350 micrometers. In some embodiments, the size of the beads is between 100 and 250 micrometers.

In some embodiments, the linker histone affinity matrix is prepared by a process comprising a) oxidizing cellulose beads having a size between 100 and 250 micrometers to yield activated cellulose beads;
b) washing the activated cellulose beads;
c) preparing a concentrated solution of the linker histone;
d) incubating the activated cellulose beads with the concentrated solution of the linker histone; and
e) blocking any free CHO groups on the activated cellulose beads.

In some embodiments, the process further comprises f) washing the activated cellulose beads with buffer.

In some embodiments, in step a) the cellulose beads are in an aqueous suspension and oxidized with NaIO. In some embodiments, in step b), the activated cellulose beads are washed with sodium bicarbonate, hydrochloric acid and water. In some embodiments, step c) comprises dialyzing a solution of the linker histone and concentrating the dialyzed solution in 0.1 M $NaHCO_3$ at pH 7-9. In some embodiments, the dialyzed solution is concentrated in 0.1 M $NaHCO_3$ at pH 8. In some embodiments, in step d) the incubation is performed for 3-5 hours at 15-30° C. In some embodiments, in step d) the incubation is performed for 4 hours at room temperature. In some embodiments, in step e) the blocking step comprises adding 1 M ethanolamine to the activated cellulose beads and reacting for 30 minutes to 2 hours at 15-30° C. In some embodiments, in step f) the activated cellulose beads are washed with TBS buffer.

Also provided are chromatography columns with an affinity matrix comprising a linker histone for larger-scale isolation of circulated cfDNA. Such chromatography column may be present as constructive part an apheresis device or other extracorporeal therapy device or apparatus and may be included to blood or plasma extracorporeal circuit; the column may be recharged independently from other part of such device or apparatus. The apheresis device may be one described in International Patent Publication No. WO2019/053243, incorporated by reference herein in its entirety.

Without wishing to be bound by theory, epigenetic biomarkers of cancer, and other diseases, can manifest as modifications of histones in circulating nucleosomes, including methylation and acetylation. Certain cfDNAs may have an origin in cancer cells with such epigenetic biomarkers. Use of linker histones provides for improved isolation of cfDNA with high quality and amount that are relevant for diagnostic, monitoring and selection of type of therapy of cancer, and other diseases.

In some embodiments of the above aspects, the biological sample comprises a biofluid (e.g., blood, serum, plasma, lymph, urine, cerebrospinal fluid (CSF), endometrial fluid, saliva, tear fluid, synovial fluid, sputum). The sample can be menstrual blood. In certain embodiments, the biological sample comprises stool or breath (e.g., condensed breath). In certain embodiments, the condensed breath is an extract of condensed breath, a purification of condensed breath, or a dilution of condensed breath. Condensed breath samples may be particularly useful to detect cfDNAs found in lung cancer tissue that are exhaled. Trace amounts of cfDNA can be obtained from the condensed breath samples, and amplified with highly sensitive quantitative PCR techniques.

In various embodiments in which the biological sample comprises condensed breath, one or more of the following methods is performed for analyzing the released DNA: DNA sequencing (e.g., tag-adapted bisulfate genomic DNA sequencing (tBGS) for mapping of DNA methylation), methylated DNA sequencing analysis, polymerase chain reaction (PCR), targeted NGS, nested PCR with subsequent sequencing, and pyrosequencing.

Various methods can be undertaken to prepare the biological samples and the biofluid samples. The samples may be homogenized (if solid or semi-solid), suspended in a buffer, diluted, subjected to reactions to precipitate proteins and DNA, etc.

In some embodiments, releasing the cfDNA comprises contacting the complex with a protease. The protease may be effective to specifically hydrolase peptide bounds of the linker histone protein while leaving the cfDNA intact. In a specific embodiment, the protease is proteinase K.

In some embodiments, releasing the cfDNA further comprises purifying the cfDNA. Such purification may be effective to remove non-DNA compounds, such as histone proteins and other protein contaminants. In some embodiments, purification comprises phenol-chloroform extraction or by extraction with phenol, chloroform, and isoamyl alcohol. In a specific embodiment, releasing the cfDNA comprises purifying the cfDNA by extraction with a 25:24:1 ratio of phenol, chloroform, and isoamyl alcohol. In various embodiments, releasing the purification further comprises ethanol precipitation. In various embodiments, purification comprises treating the cfDNA with sodium iodine, followed optionally by isopropanol precipitation, and optionally followed by ethanol precipitation. In various embodiments, a chelating resin (e.g., Chelex-100 as described in Noda et al., J. Coastal Life Medicine, 2014, 2(6): 501-504) is used to purify the cfDNA. In various embodiments, silica-based methods (e.g., QIAamp® DNA Mini and Blood Mini kits) may be used to further purify the cfDNA (e.g., by selecting some DNA fractions).

In some embodiments, the linker histone is not immobilized. The linker histone may form a complex with the cfDNA. In some embodiments, the step of separating of the complex of cfDNA with linker histone comprises capturing of the complex with affinity matrix or column with an immobilized anti-histone antibody. In some embodiments, the step of isolation of the complex of cfDNA with the linker histone comprises capturing of the complex with an affinity matrix comprising an immobilized specific anti-histone aptamer, or a column comprising an immobilized specific anti-histone aptamer. In some embodiments, the step of isolation of the complex of cfDNA with linker histone comprises capturing of the complex with affinity matrix or column comprising an immobilized specific histone-binding moiety. In some embodiments, the step of isolation of the complex of cfDNA with linker histone comprises centrifugation or sedimentation or filtration.

In some embodiments, the step of analyzing the released cfDNA comprises performing one or more of DNA sequencing (e.g., targeted NGS, whole-genome NGS), methylated DNA sequencing analysis, polymerase chain reaction (PCR), MIDI-Activated Pyrophosphorolysis (MAP), personalized analysis of rearranged ends (PARE), mass spectrometry, DNA quantification (e.g., quantitative or semi-quantitave), and DNA electrophoresis. In a specific embodiment, the PCR is digital PCR. In a specific embodiment, the digital PCR is BEAMing. In a specific embodiment, the PCR is co-amplification at lower denaturation temperature PCR (cold PCR). In some embodiments, the step of analyzing the released cfDNA comprises PCR-single strand conformation polymorphism analysis (PCR-SSCP) followed by direct sequencing. In a specific embodiment, the PCR is multiplex digital PCR (dPCR) or Intplex allele-specific PCR. Also, see, for example, Finotti A, Allegretti M, Gasparello J, et al. Liquid biopsy and PCR-free ultrasensitive detection systems in oncology (Review). Int J Oncol. 2018; 53(4):1395-1434. doi:10.3892/ijo.2018.4516.

DNA sequencing may include some amplification of the cfDNA in the sample so as to improve overall sensitivity and accuracy. The DNA sequencing may be performed in a high-throughput manner. The DNA sequencing may be performed in a quantitative manner, or semi-quantitative manner. In various embodiments, DNA sequencing may be used to identify the presence of a detectable amount of the cfDNA, and is paired with another method to quantify the cfDNA if such cfDNA is present in the sample.

PCR can be performed in a quantitative manner by various methods known in the art (e.g., qPCR and digital PCR (dPCR)). Primers and probes for PCR can be prepared based on the results of DNA sequencing. Alternatively, primers and probes can be prepared to detect cfDNAs of known sequence that are, or are suspected of, being associated with a particular disease.

In some embodiments, the cfDNA is nucleosome-bound cfDNA, exosome-bound cfDNA, and unbound cfDNA. In some embodiments, the unbound cfDNA comprises dsDNA, ssDNA and oligonucleotides.

In some embodiments, the released cfDNA is analyzed to diagnose a disease. In some embodiments, the released cfDNA is analyzed to monitor a disease. In some embodiments, the method further comprises selecting a therapy for a disease.

In various embodiments of the aspects described throughout this application, the disease may be a cancer. The cancer may be, for example, but without limitation a cancer of the breast, colon, lung, prostate, kidney, pancreas, brain, bones, ovary, testes, or a lymphatic organ. The methods of the invention may be used to detect the presence of the cancer, to estimate the size of any tumors present, to diagnose the "stage" of the cancer, and/or to provide information useful in preparing a treatment plan for the cancer.

In another aspect is provided a method of treating a patient with a disease characterized by elevated circulating levels of a cfDNA, the method comprising isolating the cfDNA according to any of the above aspects and embodiments, determining if the amount of isolated cfDNA is elevated as compared to the level of the cfDNA isolated from a normal healthy subject or a subject who does not have the disease, and administering a therapeutic compound to the patient to treat the disease. The therapeutic compound may be a compound already known to be effective against the disease. For example, if cfDNA known to be elevated in breast cancer is elevated in the patient's biofluid sample, chemotherapeutic agents appropriate for treating breast cancer can be administered. Reference ranges for the cfDNA amount in normal healthy patients (of comparable age, gender, weight, health status, etc.) may be used as the basis for comparison. In certain embodiments, it may be preferred to not use a normal healthy patient as the basis for comparison. For instance, cfDNA ranges associated with different stages of a cancer (e.g., stage I colon cancer, stage II colon cancer, stage III colon cancer, stage IV colon cancer) can be beneficial to diagnose the disease. cfDNA ranges associated with different stages of pre-diabetes and diabetes progression may be appropriate for use in diagnosing the stage of disease progression and for providing information on appropriate treatment. The patient's own prior cfDNA levels can be used as a basis for comparison to assess overall progression of the disease or condition, as in whether the disease or condition is advancing or undergoing remission.

Additionally, various different biofluid samples from the patient may be assayed according to the methods described herein. There may be different amounts of cfDNA in each sample (e.g., in each of urine, blood, and sputum) that may provide specific information on disease progression. An increase of cfDNA in blood, without a concomitant increase in urine, may be informative of how disease or condition is progressing.

In some embodiments, the method steps are repeated, or undertaken on a schedule. The method steps may be conducted twice a day, every day, every two days, every three days, every four days, every five days, every six days, every week, every eight days, every nine days, every 10 days, every 11 days, every 12 days, etc. Samples of blood may be taken from the patient and tested for levels of cfDNA to assess the frequency of conducting the methods of treatment. Comparisons may be made among the various cfDNA levels reported by the assay to assess whether the treatment plan is effective and/or if changes to the treatment plan are needed. For example, the amount of a therapeutic compound can be increased if the cfDNA levels in the patient are increasing. Conversely, if the therapeutic compound has many adverse or debilitating side effects and there is a substantial decrease in the cfDNA levels, the amount and/or frequency of dosing the therapeutic compound can be reduced.

In some embodiments, the therapeutic compound is administered to the patient only if the amount of isolated cfDNA is elevated as compared to the level of the cfDNA isolated from a normal healthy subject or a subject who does not have the disease.

In another aspect is provided a method of treating a patient with a disease characterized by elevated circulating levels of a cfDNA, the method comprising isolating the cfDNA according to the method of any of the above aspects and embodiments, determining if the amount of isolated cfDNA is elevated as compared to the level of the cfDNA isolated from a normal healthy subject or a subject who does not have the disease, and reducing the level of the cfDNA in the patient with the disease. In some embodiments, the therapeutic compound is administered to the patient only if the amount of isolated cfDNA is elevated as compared to the level of the cfDNA isolated from a normal healthy subject or a subject who does not have the disease.

In certain embodiments, the method further comprises conventionally treating the disease. Conventional means to treat the disease can include one or more of surgery, administration of drugs, or even making alterations to diet and exercise routines.

In some embodiments, the cfDNA is present in the blood, and the reduction of the level of the cfDNA is performed by an apheresis procedure. Various modes of apheresis can be undertaken, such as those described in PCT/EP2018/075014, which is incorporated by reference herein in its entirety.

In some embodiments, the method is effective to detect one or more of multiorgan failure, a neurodegenerative disease (e.g., Alzheimer's disease), cancer, sepsis, septic kidney injury, irradiation induced toxicity (e.g., acute radiation syndrome), and chemotherapy-related toxicity.

In some embodiments, the patient has a disease which may be cancer, metastatic cancer, acute organ failure, organ infarct, hemorrhagic stroke, graft-versus-host-disease (GVHD), graft rejection, sepsis, systemic inflammatory response syndrome (SIRS), cytokine releasing syndrome (CRS), multiple organ dysfunction syndrome (MODS), irradiation induced toxicity (e.g., acute radiation syndrome), chemotherapy-related toxicity, traumatic injury, pro-inflammatory status in aged individuals, diabetes, atherosclerosis, neurodegenerative disease, autoimmune disease, eclampsia, preeclampsia, infertility, coagulation disorder, asphyxia, drug intoxication, a poisoning or infection.

In some embodiments, the method is effective to detect a disorder in a patient, wherein the disorder may be cancer, metastatic cancer, acute organ failure, organ infarct (including myocardial infarction and ischemic stroke, hemorrhagic stroke, autoimmune disorders, graft-versus-host-disease (GVHD), graft rejection, sepsis, systemic inflammatory response syndrome (SIRS); cytokine releasing syndrome (CRS); multiple organ dysfunction syndrome (MODS); graft-versus-host-disease (GVHD), traumatic injury, proinflammatory status in aged individuals, diabetes, atherosclerosis, neurodegenerative disease, autoimmune disease, eclampsia, preeclampsia, infertility, coagulation disorder, pregnancy-associated complications, asphyxia, drug intoxication, a poisoning or infection. In some embodiments, the patient is in need of treatment of the disorder.

In various embodiments, the disease or condition is a neurodegenerative disease or condition, a cancer, a chemotherapy-related toxicity, an irradiation induced toxicity, an organ failure, an organ injury, an organ infarct, ischemia, an acute vascular event, a stroke, graft-versus-host-disease (GVHD), graft rejection, sepsis, systemic inflammatory response syndrome (SIRS), cytokine releasing syndrome (CRS), multiple organ dysfunction syndrome (MODS), a traumatic injury, aging, diabetes, atherosclerosis, an autoimmune disorder, eclampsia, pre-eclampsia infertility, a pregnancy-associated complication, a coagulation disorder, asphyxia, drug intoxication, a poisoning or an infection. The methods described herein may be particularly useful to detect forms of these diseases that may be difficult to detect.

In addition, the methods may be useful to stage the disease or to determine if multiple diseases are present in the same patient. The methods may also be useful to provide prophylactic treatment if the amount of cfDNA in the biofluid sample reflects an early stage of the disease that is not yet showing other symptoms. The method may be used to monitor the spreading and/or distribution of a transgene inside a human who has consumed a GMO product. The method may also be used to monitor the persistence of a transgene inside a human who has consumed a GMO product.

In various embodiments, the subject is a human. In various embodiments, the patient is a human. The subject can be a mammal, e.g., a farm animal (e.g., a horse, a pig, a goat), or a pet. The mammal can be an adult or a child. The methods described herein may be particularly helpful to diagnose the state of disease in animals that cannot otherwise communicate their symptoms. The method may also be helpful in agriculture applications in assessing overall health status of farm animals. The method may be used to monitor the spreading and/or distribution of a transgene inside a transgenic animal, or in an animal subjected the contact with a GMO product. The method may also be used to monitor the persistence of a transgene inside a transgenic animal, or in an animal subjected the contact with a GMO product. For example, blood samples from a herd of animals can be pooled, with an overall cfDNA assessment undertaken. Changes to animals' diet and care can be made, with a followup assessment performed again from blood samples pooled from the herd to assess the effect on changing the diet. The method may also be helpful in assessing changes in the health of individual high-value animals, such as race horses and animals used for breeding.

The methods described herein can be accommodated into a personalized medicine regimen. The personalized medicine regimen can even be applied to people who are generally healthy but wish to avoid disease and improve their overall health. For example, if cfDNA associated with metabolic syndrome is elevated, the person can be prescribed a suitable diet and/or exercise regimen to prevent or reverse hypertension, diabetes, coronary artery disease, etc.

EXAMPLES

The present invention is also described and demonstrated by way of the following examples. However, the use of these and other examples anywhere in the specification is illustrative only and in no way limits the scope and meaning of the invention or of any exemplified term. Likewise, the invention is not limited to any particular preferred embodiments described here. Indeed, many modifications and variations of the invention may be apparent to those skilled in the art upon reading this specification, and such variations can be made without departing from the invention in spirit or in scope. The invention is therefore to be limited only by the terms of the appended claims along with the full scope of equivalents to which those claims are entitled.

Example 1: Preparation of Histone H1.3 Affinity Matrix and Affinity Column

The histone H1.3 affinity matrix and affinity column were prepared as follows: cellulose beads (bead size of 100-250 micrometers, Sigma-Aldrich) were oxidized with sodium metaperiodate. To accomplish this, an aqueous suspension of the beads (3 g, 5 mL) and NaO, (0.1 g, 0.5 mmol) in 10 mL of water was shaken at room temperature for 4 h. The activated beads were collected and washed with 1 M sodium bicarbonate, 0.1 M hydrochloric acid and 200 mL of water. A solution of recombinant human histone H1.3 (≥98% purity, Institute of Bioorganic Chemistry, Moscow) was dialyzed and concentrated (10 mL; 5 mg/mL) in 0.1 M $NaHCO_3$ (pH 8).

Then the solution was incubated with oxidized beads (5 ml) at room temperature for 4 h with stirring. After the incubation, 1 M ethanolamine (1.5 mL) was added to the activated beads suspension (15 ml) to block the free CHO groups; the reaction continued for 1 h at room temperature. The resulting cellulose beads with immobilized histone H1.3 were washed three times with TBS buffer to remove soluble protein contaminants and to provide histone H1 affinity matrix. Polycarbonate columns of 2 mL-30 mL volume were loaded (to 70-90% of the volume) with the cellulose matrix with immobilized histone H1 to provide histone H1 affinity column.

Example 2: Preparation of Histone 111.0 Affinity Matrix

A solution of recombinant human histone H1.0 (≥96% purity, BioLabs Inc, Cat #M2501S) having protein sequence TENSTSAPAAKPKRAKASKKSTDHPKYSDMIVAAI-QAEKNRAGSSRQSIQKYIKSHYKV GENADSQIKL-SIKRLVTTGVLKQTKGVGASGSFRLAKSDEPKKS-VAFKKTKKEIKKVAT PKKASKPKKAASKAPTK-KPKATPVKKAKKKLAATPKKAKKPKTVKAK-PVKASKPKKA KPVKPKAKSSAKRAGKKK (SEQ ID NO: 2) was used. Before immobilization, the solution of the ligand was dialyzed and concentrated (5 mg/mL) in 0.2 M borate buffer, pH 8.2

Cross-linked agarose beads (Sepharose 4FF, GE Health Care, Cat. No. 17-149-01, bead size range: 45-165 micrometers) was washed with a 20-fold volume excess of distilled water on a glass filter. Then the washed suspension of the beads was squeezed using the peristaltic pump and weighed. Distilled water was added and a 50% suspension was prepared. The sedimented beads was washed on a glass filter with a cold (4° C.) solution containing 4M KOH and 1.6M $KH_2PO_4$ (4 ml of the solution per 1 ml of the agarose bead gel).

The prepared 50% suspension of the agarose beads in a solution of 4 M KOH and 1.6 M $KH_2PO_4$ was placed in an ice bath. A solution of BrCN in dioxane (1 g/mL) was added to the suspension (0.05 g BrCN per 1 mL of 4FF Sepharose) and incubated for 7 min. Then the activated matrix was washed with 5-fold volumes excess of distilled water and 1 volume of 0.2 M borate buffer, pH 8.2. Prepared histone H1.0 solution (5 mg/mL) was added to 2.5 mL of the activated matrix for immobilization (the ligand load was calculated as 10 mg per 1 mL of the activated matrix).

The mix of the activated matrix and the ligand was incubated on a shaker at a temperature of 20° C. for 2 hours. The matrix with immobilized histone was washed with 3 volumes of 0.2 M pH 8.2 borate buffer. Then, 1 volume of a 1M solution of ethanolamine pH 8.0 was added and incubated for 1.5 hours on a shaker at a temperature of 20° C. Then, to remove soluble matters the resulting affinity matrix was washed successively with: a 20-fold volume excess of distilled water; a 10-fold volume excess of phosphate buffer (pH 7.5); a 10-fold volume excess of citrate buffer (pH 2.5); 20-fold volumes of distilled water. The finished affinity matrix was added with phosphate-buffered saline (PBS), pH 7.4 to obtain 50% suspension and then added with preservative (sodium azide, up to 0.02%). The agarose matrix with immobilized histone H1.0 was stored at +4° C. Before use, the affinity matrix was washed with 10-volume excess of 0.9% nuclease free sodium chloride solution.

Example 3: Preparation of Histone H1 Affinity Matrix and Affinity Column for Capture of Cell Free DNA from Biological Sample The histone H1 affinity matrix and affinity column were prepared as follows: cellulose beads (bead size of 100-250 micrometers, Sigma-Aldrich) were oxidized with sodium metaperiodate. To accomplish this, an aqueous suspension of the beads (3 g, 5 mL) and NaIO, (0.1 g, 0.5 mmol) in 10 mL of water was shaken at room temperature for 4 hours. The activated beads were collected and washed with 1 M sodium bicarbonate, 0.1 M hydrochloric acid and 200 mL of water. A solution of recombinant human histone H1.3 (≥98% purity, manufactured by Shemyakin Institute of Bioorganic Chemistry, Moscow) was dialyzed and concentrated (10 mL; 5 mg/mL) in 0.1 M $NaHCO_3$ (pH 8). The solution was then incubated with oxidized beads (5 ml) at room temperature for 4 hour with stirring. After the incubation, 1 M ethanolamine (1.5 mL) was added to the activated beads suspension (15 ml) to block the free CHO groups; the reaction continued for 1 hour at room temperature. The resulting cellulose beads with immobilized histone H1 were washed three times with TBS buffer to remove soluble protein contaminants and to provide histone H1 affinity matrix. Polycarbonate columns of 1-2 mL volume were loaded to 70-90% of the volume with the cellulose matrix with immobilized histone H1.

Example 4: Capture of Cell Free DNA from Plasma Using Histone H1 Affinity Matrix Plasma from three cancer patients with metastatic gastric adenocarcinoma was prepared by collecting blood into EDTA tubes. Plasma was separated by double centrifugation (800 g for 10 min, separation, and 1600 g for 10 min) Plasma aliquots were frozen at −70° C.

Cell free DNA was isolated from 1 ml of plasma of each patient according manufacturer protocol using Abeam ab156893 DNA Isolation Kit—Plasma/Serum, QIAamp Circulating Nucleic Acid Kit or with histone H1 affinity matrix using following protocol.

1 ml of patient plasma was mixed with 250 mkl of cellulose matrix with immobilized histone H1 prepared as specified in Example 1 and incubated for 30 m at room temperature under gentle shaking. After incubation the histone H1 affinity matrix was sedimented by centrifugation for 10 minutes at 2,000 g using a refrigerated centrifuge. The pellet was diluted by phosphate buffer containing proteinase K (BioLabs Cat. No. P8107S) and SDS (Sigma) up to final concentration of 400 mkg/ml and 1% respectively and incubated for 30 min at 37° C. in 1 ml reaction volume. Samples were placed on ice for 5 min, then extracted with an equal volume of phenol-chloroform-isoamyl alcohol (25:24:1) (Sigma-Aldrich) and centrifuged for 10 min at 14,000 g. The aqueous phase was precipitated overnight with 1/10 volume of 3 M NaOAc and 2.5 volume of 100% ethanol at −20° C. The DNA pellet was washed with ethanol, air-dried and resuspended in 100 µl of dd $H_2O$. Quantification of DNA in resulting samples were performed using Qubit 3.0. fluorimeter and Qubit dsDNA HS Assay Kit according manufacturer instructions. The human beta globin, ALU and c-MYC sequences in cell free DNA was quantified in each sample using RT-PCR (iCycler iQ5b Bio-Rad) with human beta globin primer CAACTTCATCCACGTTCACC (SEQ ID NO: 5), c-MYC primer TGAGGAGACACCGCCCAC (SEQ ID NO: 6) and ALU primer CATGGTGAAACCCCGTCTCTA (SEQ ID NO: 7). 1% Agarose gel electrophoresis E-gel system was used to visualize cell free DNA electrophoretic pattern.

The results of quantification of cell free DNA in plasma of three cancer patients collected with three different methods are presented in Table 1 below:

TABLE 1

| | Cell free DNA concentration, ng/ml | | |
|---|---|---|---|
| | H1 matrix protocol | QIAamp | ab156893 |
| Patient 1 | 173.7 | 34.7 | 43.9 |
| Patient 2 | 213.4 | 51.8 | 58.7 |
| Patient 3 | 141.2 | 27.5 | 17.3 |

The data presented above clearly confirm that the above protocol using H1 matrix yields significantly higher cell free DNA from patient plasma samples. The results of quantification of ALU, cMYC and human b-globin sequences in cell free DNA from plasma of three cancer patients collected with three different methods are presented in Table 2 below:

TABLE 2

| | H1 column | | | QIAamp | | | ab156893 | | |
|---|---|---|---|---|---|---|---|---|---|
| Sample | Alu | C-myc | β-glob | Alu | C-myc | β-glob | Alu | C-myc | β-glob |
| Patient 1 | 17.19 ± 0.703 | 21.27 ± 0.159 | 21.86 ± 0.013 | 16.13 ± 0.753 | 24.06 ± 0.732 | 23.87 ± 0.267 | 16.98 ± 0.562 | 23.18 ± 0.006 | 23.55 ± 0.321 |
| Patient 2 | 10.83 ± 0.035 | 26.0 ± 0.214 | 27.76 ± 0.153 | 10.36 ± 0.051 | 27.78 ± 0.305 | 28.62 ± 0.278 | 12.3 ± 0.117 | 29.02 ± 0.155 | 28.89 ± 0.211 |
| Patient 3 | 10.64 ± 0.132 | 25.33 ± 0.141 | 26.98 ± 0.012 | 11.38 ± 0.046 | 28.61 ± 1.033 | 30.26 ± 30.26 | 15.24 ± 0.11 | 30.56 ± 1.247 | 28.14 ± 0.224 |

The data presented above clearly confirm that molecular probing of ctDNA collected using the above H1 matrix protocol can detect specific gene sequences with significantly higher sensitivity.

Example 5, Isolation of ctDNA from a Patient with Cancer Followed by Subsequent Identification of DNA-Biomarker to Guide Options for Treatment of Cancer A 57-year-old male patient was diagnosed with non-small cell lung cancer (NCLS) after he had ceased smoking for 20 years. The patient had a 4×4.2 cm tumor lesion in the right tang. PET scan show than the lesion is active. Tumor tissue obtained by fine-needle aspiration confirmed NSCLC and was determined to be bronchioalveolar adenocarcinoma. The tissue biopsy was insufficient for biomarker testing and the patient was reluctant to undergo surgery. To guide treatment options, the patient's blood is sampled to a EDTA Vacutainer tube. Plasma is routinely separated from blood cells with centrifugation.

0.5 mL sample of plasma is applied to 2 mL affinity column prepared according to Example 3. After the plasma passes through the column completely, the column affinity matrix (with captured cfDNA) is transferred to 10 mL conical tube. The affinity matrix is sedimented by centrifugation for 20 min at 3,000 g using a refrigerated centrifuge. The sediment (pellet) is suspended 1:1 (v/v) in an enzyme reaction solution to lyse/hydrolyze the proteins and to liberate DNA from histone-DNA complex. The enzyme reaction solution is prepared by mixing (1:30, v/v) papain liquid (16-40 units/mg protein, Sigma-Aldrich, St. Louis, MO) and lysis buffer with pH 7.6 (10 mM Tris, 10 mM KCl, 1.0 mM $MgCl_2$, 0.5M NaCl, 2 mM EDTA) with 1.0% SDS.

After 1 h incubation at 50° C. with shaking, NaI solution (7.6 M NaI, 20 mM $Na_2$ EDTA, 40 mM TrisHCI (p1-18.0) is added to the lysate to the final concentration of 4.5M NaI and 0.4% SDS, and is followed by the addition of equal volume of isopropanol. After centrifugation at 10,000 g for 10 min, the pellet is resuspended in 40% isopropanol (w/v) and then repeatedly centrifugated under same conditions for 5 min. The precipitate is washed with the 70% ethanol, vacuum-dried for 3 min and suspended in TE buffer (pH 8.0).

Isolated DNA is tested with Target Selector™ assays specific for the EGFR activating mutations, L858R and exon 19 deletion (De119), or the 1790M mutation, which uses real-time PCR, Sanger sequencing and next-generation sequencing (NGS) and confers possible resistance to EGFR tyrosine kinase inhibitors (see, for example, Poole et al., A concordance study of the ArcherDX Reveal™ ctDNA 28 NGS panel and Biocept's Target Selector™ mutation assay using ctDNA collected in Biocept CEE-Sure™ blood collection tubes [abstract]. In: Proceedings of the American Association for Cancer Research Annual Meeting 2017; 2017 Apr. 1-5; Washington, DC. Philadelphia (PA): AACR; Cancer Res 2017; 77(13 Suppl): Abstract nr 762. doi: 10.1158/1538-7445.AM2017-762).

The liquid biopsy detection of EGFR L858R allows to determine mutant allele frequency (MAF). MAF of 9% is considered to be the threshold value in L858R detection and prescribing treatment (e.g., with erlotinib for about 24 months). Lung scans are conducted to determine whether the lesion diminished.

Example 6: Preparation of Histone 115 Affinity Magnetic Beads (Matrix) for Capture of cfDNA from a Biological Sample To obtain monomer solution 300 mg and 100 mg of acrylamide and N,N'-Methylenebis (acrylamide), both were o"reagent grade, ≥99%, Merck, respectively, were dissolved in 2 ml of 0.15 M sodium chloride solution. To obtain a magnetic polyacrylamide beads with immobilized histone H5, 0.6 mg of recombinant (anser) histone H5 (≥85% purity, Cat. No. MBS1207138, MyBioSource, USA) having protein sequence TDSPIPAPAPAAKPKRARAPRKPASHPTYSE-MIAAAIRADKSRCiGSSRQSIQKYVKSHYK VGQHA-DLQIKLAIRRLLTTGVLKQTKGVGASGSFRLAKGD-KAKRSPAGRKKKKKAARK STSPKKAARPRKAR-SPAKKPKAAARKARKKSRASPKKAKKPKTVKA-KSLKTSKPKKAR RSKPRAKSGARKSPKKK (SEQ ID NO: 3) was added to this solution. Before adding, the solution of the hi stone was dialyzed and dried under vacuum to obtain powder.

In a container with 100 ml of hexane and 0.5 ml of the emulsifier sorbitane trioleate (Span 85, Sigma-Aldrich), nitrogen gas was fed under a pressure of 0.2-1 atm through a tube with a cross section of 0.7 mm so as to create intensive stirring for 8 minutes. 1.0 mL of 0.9% sodium chloride solution with containing 200 mg of iron (II, III) oxide powder (particle size<5 μm, 95%, Sigma-Aldrich) and 10 mg of ammonium persulfate (≥98%, Sigma-Aldrich) were placed to the polymerization flask. After 1-2 minutes, 2 mL of a solution containing monomers and ligand (acrylamide; N,N'-Methylenebis (acrylamide) and recombinant histone H5), and 20 μl of NNN'N'-tetramethyl ethylenedi amine (≥99.5%, Sigma-Aldrich) were added.

After the polymerization was completed, the beads were washed with acetone and physiological saline with a Tween-20 detergent (0.05%) for 10-15 min to remove unreacted monomers, emulsifier, histone and hexane: The beads had a standard spherical shape with a gel particle size of 10-100 microns. The ratio of polymeric support:iron was equal 2:1 (by dry weight).

The present invention is not to be limited in scope by the specific embodiments described herein. Indeed, various modifications of the invention in addition to those described herein will become apparent to those skilled in the art from the foregoing description. Such modifications are intended to fall within the scope of the appended claims. It is further to be understood that all values are approximate, and are provided for description.

Patents, patent applications, publications, product descriptions, and protocols are cited throughout this application, the disclosures of which are incorporated herein by reference in their entireties for all purposes.

The invention claimed is:

1. A method for isolating a cell free DNA (cfDNA) from a biological sample comprising the cfDNA, the method comprising:

(i) contacting the biological sample with a linker histone covalently immobilized on a solid support, wherein the linker histone forms a complex with the cfDNA;

(ii) separating the complex obtained in step (i) from the biological sample, and (iii) releasing the cfDNA from the complex separated in step (ii).

2. The method of claim 1, wherein the linker histone is bound to a magnetic particle.

3. The method of claim 1, wherein the biological sample is a blood sample, a serum sample, a plasma sample, a cerebrospinal fluid (CSF) sample, an endometrial fluid sample, a urine sample, a saliva sample, a lymph sample, a tear fluid sample, a synovial fluid sample, or a sputum sample.

4. The method of claim 3, wherein the biological sample is a blood sample, a plasma sample, or a serum sample.

5. The method of claim 1, wherein the linker histone is a mammalian somatic linker histone.

6. The method of claim 1, wherein the linker histone is a linker histone H1 or a linker histone H5.

7. The method of claim 6, wherein the linker histone H1 is selected from an H1.0 linker histone, an H1.1 linker histone, an H1.2 linker histone, an H1.3 linker histone, an H1.4 linker histone, and an H1.5 linker histone.

8. The method of claim 7, wherein the linker histone H1 is a human H1.3 linker histone.

9. The method of claim 7, wherein the linker histone H1 is a human H1.0 linker histone.

10. The method of claim 1, wherein the linker histone comprises an amino acid sequence which is at least 70% identical to the sequence (SEQ ID NO: 1)
MSETAPLAPTIPAPAEKTPVKKKAKKAGATAGKRKASGPP
VSELITKAVAASKERSGVSLAALKKALAAAGYDVEKNNSR
IKLGLKSLVSKGTLVQTKGTGASGSFKLNKKAASGEGKPK
AKKAGAAKPRKPAGAAKKPKKVAGAATPKKSIKKTPKKVK
KPATAAGTKKVAKSAKKVKTPQPKKAAKSPAKAKAPKPKA
AKPKSGKPKVTKAKKAAPKKK or to the sequence (SEQ ID NO: 2)
TENSTSAPAAKPKRAKASKKSTDHPKYSDMIVAAIQAEKN
RAGSSRQSIQKYIKSHYKVGENADSQIKLSIKRLVTTGVL
KQTKGVGASGSFRLAKSDEPKKSVAFKKTKKEIKKVATPK
KASKPKKAASKAPTKKPKATPVKKAKKKLAATPKKAKKPK
TVKAKPVKASKPKKAKPVKPKAKSSAKRAGKKK.

11. The method of claim 1, wherein the linker histone comprises an amino acid sequence which is at least 70% identical to the sequence (SEQ ID NO: 3)
TDSPIPAPAPAAKPKRARAPRKPASHPTYSEMIAAAIRAD
KSRGGSSRQSIQKYVKSHYKVGQHADLQIKLAIRRLLTTG
VLKQTKGVGASGSFRLAKGDKAKRSPAGRKKKKKAARKST
SPKKAARPRKARSPAKKPKAAARKARKKSRASPKKAKKPK
TVKAKSLKTSKPKKARRSKPRAKSGARKSPKKK or to the sequence (SEQ ID NO: 4)
MTESLVLSPAPAKPKRVKASRRSASHPTYSEMIAAAIRAE
KSRGGSSRQSIQKYIKSHYKVGHNADLQIKLSIRRLLAAG
VLKQTKGVGASGSFRLAKSDKAKRSPGKKKKAVRRSTSPK
KAARPRKARSPAKKPKATARKARKKSRASPKKAKKPKTVK
AKSRKASKAKKVKRSKPRAKSGARKSPKKK.

12. The method of claim 1, wherein releasing the cfDNA comprises contacting the complex with a protease.

13. The method of claim 1, wherein the separating step (ii) comprises one or more of centrifugation, sedimentation or filtration.

* * * * *